(12) United States Patent
Hohmann et al.

(10) Patent No.: US 11,466,303 B2
(45) Date of Patent: Oct. 11, 2022

(54) PRODUCTION OF STEROLS IN MODIFIED YEAST

(71) Applicant: DSM IP ASSETS B.V., Heerlen (NL)

(72) Inventors: Hans-Peter Hohmann, Kaiseraugst (CH); Regina Leber, Graz (AT); Martin Lehmann, Kaiseraugst (CH); Corinna Odar, Graz (AT); Barbara Petschacher, Graz (AT); Harald Pichler, Graz (AT); Birgit Ploier, Graz (AT)

(73) Assignee: DSM IP ASSETS B.V., Heerlen (NL)

( * ) Notice: Subject to any disclaimer, the term of this patent is extended or adjusted under 35 U.S.C. 154(b) by 858 days.

(21) Appl. No.: 16/065,274

(22) PCT Filed: Dec. 20, 2016

(86) PCT No.: PCT/EP2016/081936
§ 371 (c)(1),
(2) Date: Jun. 22, 2018

(87) PCT Pub. No.: WO2017/108799
PCT Pub. Date: Jun. 29, 2017

(65) Prior Publication Data
US 2021/0180103 A1 Jun. 17, 2021

(30) Foreign Application Priority Data

Dec. 23, 2015 (CH) .................................... 01908/15

(51) Int. Cl.
| | |
|---|---|
| *C12P 33/16* | (2006.01) |
| *C12N 1/16* | (2006.01) |
| *C12N 9/02* | (2006.01) |
| *C12N 9/10* | (2006.01) |

(52) U.S. Cl.
CPC ................ *C12P 33/16* (2013.01); *C12N 1/16* (2013.01); *C12N 9/0071* (2013.01); *C12N 9/1007* (2013.01); *C12N 9/1029* (2013.01)

(58) Field of Classification Search
CPC . C12P 33/16; C12P 33/00; C12N 1/16; C12N 9/0071; C12N 9/1007; C12N 9/1029; C12N 9/001
See application file for complete search history.

(56) References Cited

U.S. PATENT DOCUMENTS

2006/0240508 A1* 10/2006 Lang .............. C12Y 103/01072
435/61

FOREIGN PATENT DOCUMENTS

WO WO-2003-064650 A1 * 8/2003

OTHER PUBLICATIONS

Guo et al. Metabolic engineering of *Saccharomyces cerevisiae* for 7-dehydrocholesterol overproduction. Biotechnol Biofuels (2018), 11:p192.*
International Search Report for PCT/EP2016/081936 dated May 5, 2017, 4 pages.
Written Opinion of the ISA for PCT/EP2016/081936 dated May 5, 2017, 5 pages.
B. Ploier et al., "Engineering of Sterol Synthesis in Yeast", Retrieved from the Internet, Jan. 1, 2017.
C. Souza et al., "A stable yeast strain efficiently producing cholesterol instead of ergosterol is functional for tryptophan uptake, but not weak organic acid resistance", Metabolic Engineering, vol. 13, No. 5, Jun. 4, 2011, pp. 555-569.
H. Melanie et al., "A novel cholesterol-producingPichia pastoris-strain is an ideal host for functional expression of human Na,K-ATPase [alpha] 3 [beta] 1", Applied Microbiology and Biotechnology, vol. 97, No. 21, Aug. 17, 2013, pp. 9465-9478.
T. Wriessnegger et al., "Yeast metabolic engineering—Targeting sterol metabolism and terpenoid forma", Progress in Lipid Research, vol. 52, No. 3, Apr. 6, 2013, pp. 277-293.
K. Katja et al., "Steroid-transforming enzymes in fungi", Journal of Steroid Biochemistry and Molecular Biology, vol. 129, No. 1, 2012, pp. 79-91.
Hirz, M., et al., "A Novel Cholesterol-Producing Pichia Pastoris Strain is an Ideal Host for Functional Expression of Human Na,K-ATPase α3β1 Isoform," Appl. Microbiol. Biotechnol., 97, pp. 9465-9478, 2013.
Kristan, K., et al., "Steroid-Transforming Enzymes in Fungi," Journal of Steroid Biochemistry & Molecular Biology 129, pp. 79-91, 2012.
Ploier, B., "Engineering of Sterol Synthesis in Yeast," ACIB, Institut für Molekulare Biotechnologie Technische Universität Graz, Masters Thesis, 2010.
Souza, C., et al., "A Stable Yeast Strain Efficiently Producing Cholesterol Instead of Ergosterol is Functional for Tryptophan Uptake, But Not Weak Organic Acid Resistance," Metabolic Engineering, 13, pp. 555-569, 2011.
Wriessnegger, T., et al., "Yeast Metabolic Engineering—Targeting Sterol Metabolism and Terpenoid Formation," Progress in Lipid Research 52, pp. 277-293, 2013.

* cited by examiner

*Primary Examiner* — Iqbal H Chowdhury
(74) *Attorney, Agent, or Firm* — Nixon & Vanderhye, PC

(57) ABSTRACT

The present invention is related to production of a sterol mix in a modified yeast cell, wherein the amount of zymosterol present in said mix is dramatically reduced or abolished via modification of sterol acyltransferase activity within said yeast. The modified yeast cell can be used for production of vitamin D3 or derivatives and/or metabolites thereof.

Figure 1:
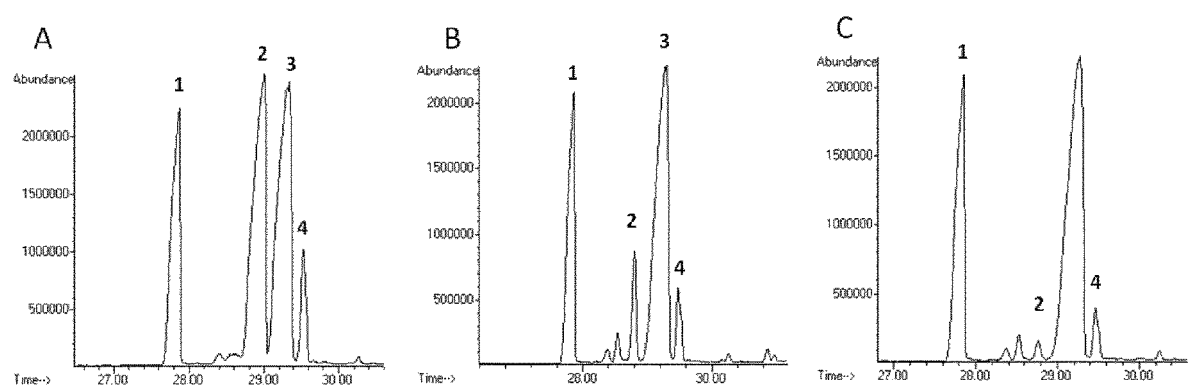

6 Claims, 4 Drawing Sheets
Specification includes a Sequence Listing.

PRODUCTION OF STEROLS IN MODIFIED YEAST

This application is the U.S. national phase of International Application No. PCT/EP2016/081936 filed Dec. 20, 2016 which designated the U.S. and claims priority to CH Patent Application No. 01908/15 filed Dec. 23, 2015, the entire contents of each of which are hereby incorporated by reference.

The present invention is related to production of a sterol mix in a modified yeast cell, wherein the amount of zymosterol present in said mix is dramatically reduced or abolished via modification of sterol acyltransferase activity within said yeast. The modified yeast cell can be used for production of vitamin D3 or derivatives and/or metabolites thereof.

Vitamin D3 (also known as cholecalciferol or calciol) can be synthesized in the skin of mammals from provitamin D3 (also known as 7-dehydrocholesterol or 7-DHC) which is product of cholesterol biosynthesis upon exposure to UV light, whereby 7-DHC is photochemically converted into provitamin D3, which isomerizes at body temperature to the biologically active form vitamin D3. In the liver, vitamin D3 is converted to the biologically inactive 25-hydroxyvitamin D3 (also known as calcidiol, calcifediol, 25-hydroxycholecalciferol, 25-OH-D3 or HyD), which is the major circulating form of vitamin D3. Further hydroxylation occurs in the kidney.

For industrial production of vitamin D3, both chemical and biotechnological synthesis is (in principle) available. Chemical synthesis starts with cholesterol isolated from e.g. wool fat which is dehydrogenated into 7-DHC, followed by UV-light exposure and further purification/extraction steps leading to vitamin D3. Alternatively, modified yeast strains can be used for producing vitamin D3 precursors, which can be isolated and further converted into vitamin D3. Excessive amounts of sterols such as the vitamin D3 precursors, including 7-DHC, are stored in intracellular organelles (so-called lipid droplets) from which they can be further isolated. The equilibrium between free sterols including the vitamin D3 precursors and those stored in the lipid droplets (in the form of sterol or steryl esters) is triggered via the action of several proteins, in particular enzymes, including sterol acyltransferases.

Normally, yeast or other fungal cells are not suitable for vitamin D3 production as such: first, starting from acetyl CoA, the natural main sterol produced by yeasts and other fungi is ergosterol instead of cholesterol. This bottleneck has been circumvented by introduction of a double-knock-out in the genes encoding ERG5 and ERG6, leading towards production of cholesta-5,7,24(25)-trienol and zymosterol in a more or less equivalent amount and only minimal production of ergosterol by such a erg5erg6 double-knock strain.

This, however, leads to a further bottleneck: only cholesta-5,7,24(25)-trienol and not zymosterol can be used as vitamin D3 precursor. Trienol is the direct precursor for 7-DHC, which can be used for vitamin D3 production. Accumulation of other sterol pathway intermediates like zymosterol is not helpful for such a production process and will have a negative impact on the production process in many ways (yield, down-stream processing, etc.).

Thus, it is an ongoing task to generate host cells, such as yeast cells, suitable for production of vitamin D3 precursors, i.e. cholesta-5,7,24(25)-trienol producing host cells, wherein the equilibrium between cholesta-5,7,24(25)-trienol and zymosterol is shifted towards cholesta-5,7,24(25)-trienol, which is expected to lead also to an increase in the amount of vitamin D3 precursors such as 7-DHC produced by such a yeast strains which are further converted to vitamin D3 and/or derivatives or metabolites thereof. A particular metabolite which is also in focus of the present invention is 25-hydroxyvitamin D3.

Surprisingly, we now found that the composition of total sterols within a cholesterol-producing yeast cell can be dramatically changed, i.e. the product ratio can be shifted towards cholesta-5,7,24(25)-trienol and/or 7-DHC instead of zymosterol to be stored in the lipid droplets by decreasing or abolishing the activity of certain sterol acyltransferases present in such yeast strains, and optionally introducing heterologous sterol-O-acyltransferases (HATs) into such yeast cell.

In particular, it has been found that by decreasing or abolishing the activity of sterol acyltransferase isoform Are2p in a cholesterol-producing yeast the amount of zymosterol could be nearly nullified (based on the total amounts of zymosterol) towards a strong increase of cholesta-5,7,24(25)-trienol as sterol compounds present in the lipid droplets. Upon further manipulation, such strains could be used for production of vitamin D3 precursors, e.g. 7-DHC.

Thus, the present invention is related to a yeast cell in which ERG5 and ERG6 are inactivated and which carries a modification in the ARE2 gene such that the activity of endogenous ARE2 is reduced or abolished, preferably abolished, said yeast cell being capable or used for production of a sterol mix comprising cholesta-5,7,24(25)-trienol and zymosterol, wherein the percentage of zymosterol within said mix is about 10% or less based on the total amount of sterols produced by said yeast and compared to a yeast cell with ARE2 activity, e.g. wherein the endogenous ARE2 is active. When using said yeast cell in a sterol production process, the percentage of cholesta-5,7,24-trienol can be increased to about 75% or more, preferably such as 77, 80, 86, 87, 90, 95% based on the total amount of sterols. Thus, the ratio of cholesta-5,7,24-trienol to zymosterol produced by said yeast is in the range of about >7 to about based on the total amount of sterols. This ratio is even more shifted towards cholesta-5,7,24-trienol when using a yeast cell in which ERG5 and ERG6 are inactivated and both ARE1 and ARE2 activity, e.g. the activity of both the endogenous ARE1 and ARE2, are reduced or abolished, preferably abolished. In such a yeast cell, the ratio might be in the range of about A to about 0, even in the range of about A to about 2 based on the total amount of sterols. When compared to a yeast cell with ARE1 and/or ARE2 activity, e.g. wherein the endogenous ARE1 and ARE2 are still active, the percentage of zymosterol is decreased by about 4-times through inactivation of ARE2. This is even higher in a strain wherein both ARE2 and ARE1 are inactivated, e.g. wherein the endogenous ARE2 and ARE1 are inactivated, i.e. the percentage is decreased by about 20-times compared to a yeast cell with ARE1 and/or ARE2 activity, e.g. wherein the endogenous ARE1 and ARE2 are still active.

In a further embodiment, the present invention relates to a yeast cell in which ERG5 and ERG6 are inactivated, wherein ARE2 activity, e.g. the activity of endogenous ARE2, within said yeast cell is reduced or abolished, preferably abolished, said yeast cell being capable or used for producing a sterol mix comprising cholesta-5,7,24(25)-trienol and zymosterol, wherein the percentage of cholesta-5,7,24-trienol within said mix is about at least 75%, preferably such as 77, 80, 86, 87, 90, 95% based on the total amount of sterols produced within said yeast cell. In one particular embodiment, the yeast cell is further modified such that the activity of ARE2 and ARE1 are both reduced or abolished, e.g. the activity of endogenous ARE2 and ARE1 are both reduced or abolished, preferably abolished, which will lead to a further increase in the percentage of cholesta-5,7,24-trienol, i.e. in the range of about 86% or more based on the total amount of sterols. Thus, compared to a cholesterol-producing yeast cell wherein ERG5 and ERG6 are inactivated but wherein ARE1 and ARE2 are still active, the amount of cholesta-5,7,24-trienol can be increased by about 2-times (in a yeast cell with reduced or abolished ARE1 and ARE2 activity, preferably abolished, e.g. in a yeast cell wherein both the activity of endogenous ARE1 and ARE2 is reduced or abolished, preferably abolished).

The yeast cells of the embodiments described herein might be used in a process for production of vitamin D3 precursors, such as e.g. 7-DHC. Thus, the present invention is directed to a yeast cell, in which ERG5 and ERG6 are inactivated, wherein the yeast expresses a heterologous enzyme selected from EC 1.3.1.72, in particular a heterologous enzyme having sterol Δ24-reductase activity, preferably a vertebrate enzyme, and wherein ARE2 activity is reduced or abolished, preferably abolished, e.g. the activity of endogenous ARE2 is reduced or abolished, preferably abolished, said yeast being capable or used for production of a sterol mix comprising 7-DHC and zymosterol, wherein the percentage of zymosterol within said mix is in the range of about 2 or 3% or less.

Using such yeast strain, the percentage of 7-DHC present in said mix is in the range of about 87% or more, preferably such as 88, 90, 95, 98% based on the total amount of sterols. In one particular embodiment, the yeast cell is further modified such that ARE2 and ARE1 activity are both reduced or abolished, preferably abolished, e.g. the activity of endogenous ARE2 and ARE1 are both reduced or abolished, preferably abolished, which will lead to a further increase in the percentage of 7-DHC, i.e. in the range of about 90% or more based on the total amount of sterols. When compared to a yeast cell having ARE2 and ARE1 activity, e.g. wherein the endogenous ARE2 and ARE1 are both still active, the percentage of zymosterol is decreased by about 15-times through inactivation of ARE2 and even more in comparison to a reduction or abolishment of both ARE1 and ARE2.

In a particular embodiment, the invention is directed to a process for the production of a sterol mix wherein one of the yeast cells as described before is used and wherein the percentage of zymosterol present in said sterol mix is decreased, i.e. is in the range of about 10% or less based on the total amount of sterols. Yeast cells used for such process are characterized via inactivation of ERG5 and ERG6 and with abolished or reduced ARE2 activity, e.g. abolished or reduced activity of endogenous ARE2, preferably abolished activity. In a particular embodiment, such a yeast cell expresses a heterologous enzyme selected from EC 1.3.1.72, such as a heterologous C24-reductase that is active on lathosterol, zymosterol, or trienol, in particular a plant or vertebrate sterol Δ24-reductase and/or comprises further modification, i.e. abolished or reduced activity of ARE1, e.g. abolished or reduced activity of endogenous ARE1, preferably abolished activity.

If one of the yeast cells as described herein is used for production of vitamin D3 precursors comprising 7-DHC, the expression of a heterologous C24-reductase that is active on lathosterol, zymosterol, or trienol, in particular a plant or vertebrate sterol Δ24-reductase, preferably a vertebrate sterol Δ24-reductase, is preferred within said cell. Thus, the present invention is related to a yeast cell as described before for the production of vitamin D3 precursors comprising 7-DHC, wherein a heterologous C24-reductase is expressed, said heterologous C24-reductase being active on lathosterol, zymosterol, or trienol.

In a particular embodiment, the invention relates to a process for improving a yeast cell towards production of cholesta-5,7,24-trienol and/or 7-DHC, wherein a yeast cell in which ERG5 and ERG6 are inactivated is further modified through reduction or abolishment, preferably abolishment, of ARE2 or ARE2 and ARE1, e.g. reduction or abolishment of endogenous ARE2 or ARE2 and ARE1 activity, wherein the yeast cell is improved such that the percentage of cholesta-5,7,24-trienol in the total amount of sterol produced by said yeast is increased from about 45% to about at least 75%, preferably such as 77, 80, 86, 87, 90, 95%.

In case of the production towards 7-DHC, which is to be improved in a yeast cell, a yeast cell in which ERG5 and ERG6 are inactivated is further modified through (1) reduction or abolishment, preferably abolishment, of ARE2 or ARE2 and ARE1, and (2) expression of a heterologous C24-reductase that is active on lathosterol, zymosterol, or trienol, in particular a plant or vertebrate sterol Δ24-reductas, preferably vertebrate sterol Δ24-reductase, wherein the yeast cell is improved such that the percentage of 7-DHC in the total amount of sterol produced by said yeast is increased from about 45% to at least about 87% or more, preferably such as 88, 90, 95, 98%.

As used herein, a cholesterol-producing yeast strain cannot produce ergosterol anymore but cholesterol products, including, but not limited to cholesta-5,7,24(25)-trienol, cholesta-5,8,24(25)-trienol, cholesta-7,24(25)-dienol, 7-DHC or zymosterol. In particular, this is achieved via introduction of erg5erg6 double-knock out. By furthermore preferably expression of a heterologous C-24 reductase that is active on lathosterol, zymosterol, or trienol (e.g. cholesta-5,7,25-trienol), in particular a plant or vertebrate sterol Δ24-reductase in such a background, production of 7-DHC is enhanced (see e.g. WO 2003064650).

The terms "ARE1" and "Are1p", "ARE2" and "Are2p", "ERG5" and "Erg5p", "ERG6" and "Erg6p" are used interchangeably herein and refer the polypeptide encoded by the respective genes are1, are2, erg5, and erg6. For the purpose of the present invention, the cholesterol-producing yeast cell is modified such that it does shows reduced or abolished activity of ARE2 or both ARE2 and ARE1, e.g. either carries a modification in either endogenous ARE2 or both endogenous ARE2 and ARE1, leading to reduced or abolished activity or ARE2 or ARE2 and ARE1.

The term "activity of ARE", such as e.g. "activity of ARE2 and/or ARE1" means catalytic activity toward conversion of acyl-CoA and cholesterol (as substrates) to CoA and cholesteryl ester (as products). Both ARE2 and ARE1 belong to EC 2.3.1.26, i.e. acyltransferases transferring fatty acyl groups from one molecule to another. Such transfer or enzymatic activity can be measured by means known to the skilled person. Acyltransferases have been isolated from different origins, including mammals, yeast or plants.

As used herein, the activity of ARE2 or ARE1 and ARE2 is reduced or abolished. This might be achieved by, e.g. introducing a mutation into the endogenous gene coding for ARE1 or ARE2. The skilled person knows how to genetically manipulate a yeast cell resulting in reduction or abolishment of ARE1 and/or ARE2 activity. These genetic manipulations include, but are not limited to, e.g. gene replacement, gene amplification, gene disruption, transfection, transformation using plasmids, viruses, or other vectors.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

Modifications in order to have the yeast cell produce less or no copies of the ARE1 or ARE2 genes and/or proteins, i.e. to have less or no ARE1 or ARE2 activity, may include the use of a weak promoter, or the mutation (e.g. insertion, deletion or point mutation) of (parts or) the ARE2 and/or ARE1 (as described herein), in particular its regulatory elements. An example of such a genetic manipulation may for instance affect the interaction with DNA that is mediated by the N-terminal region of ARE1 or ARE2 or interaction with other effector molecules. In particular, modifications leading to reduced or abolished ARE2 or ARE2 specific activity may be carried out in functional, such as functional for the catalytic activity, parts of the proteins. Furthermore, reduction or abolishment of ARE1 or ARE2 specific activity might be achieved by contacting ARE1 or ARE2 with specific inhibitors or other substances that specifically interact with ARE1 or ARE2. In order to identify such inhibitors, the ARE1 or ARE2 proteins may be expressed and tested for activity in the presence of compounds suspected to inhibit their activity.

According to the present invention, the activity of ARE1 or ARE2 is reduced. In particular, a yeast cell as described herein carries an (endogenous) ARE1 and ARE2, wherein the activity of ARE2 or of ARE2 and ARE1 is/are reduced in particular by at least 20%, preferably by at least 50, 60, 70, 80, 90%. Most preferably, as described herein, the activity is reduced by 100%, i.e. reduced to zero activity, i.e. abolished. This might apply to the activity of ARE2 only or to both the activity of ARE2 and ARE1. Abolishment of the activity might be achieved by e.g. knocking-out/deleting one or both of the genes or parts of gene(s) coding of ARE1 or ARE2.

Genes encoding ERG5, ERG6, ARE1, ARE2 or sterol Δ24-reductase (ERG4), cultivation and genetic engineering of the yeast cell as used herein are known and described in e.g. U.S. Pat. No. 7,608,421. In particular, sterol Δ24-reductase to be expressed in the yeast cell may be originated from plant or vertebrate source, preferably from vertebrate source, more preferably from human, pig, dog, mouse, rat, horse, *Danio rerio* or any known source, as long as it can be expressed within said yeast cell. Most preferably, the sterol Δ24-reductase is selected from *Danio rerio*, rat or human. The sequences expressing said sterol Δ24-reductase enzymes are publicly available, including but not limited to UniProtKB/Swiss-Prot reference Q15392, Q60HC5, Q8VCH6, Q5BQE6, Q39085 or P93472.

As used herein, the terms "C-24-reductase" or "Δ24-reductase" are used interchangeably herein. In yeast, this enzyme is encoded by erg4 and is active on the methyl-group of the carbon atom on position 24. Trienol, which does not exhibit such methyl-group on said position, is therefore not an acceptable substrate for the yeast ERG4.

A suitable yeast cell which can be used for the performance of the present invention might be selected from e.g. *Saccharomyces cerevisiae, Schizosaccharomyces* spp., *Pichia* spp., *Klyuveromyces* spp., *Hansenula* spp. or *Yarrowia lipolytica*, as long as within such a yeast cell ERG5 and ERG6 are inactivated.

In particular, the present invention features the present embodiments:

A yeast cell in which ERG5 and ERG6 are inactivated, wherein the ARE2 activity, e.g. the activity of endogenous ARE2, has been reduced or abolished, said yeast cell being used for the production of a sterol mix comprising cholesta-5,7,24(25)-trienol and zymosterol, wherein the percentage of zymosterol within said sterol mix is about 10% or less based on the total amount of sterols produced by said yeast cell.

A yeast cell in which ERG5 and ERG6 are inactivated, wherein the ARE2 activity, e.g. the activity of endogenous ARE2, has been reduced or abolished, said yeast cell being used for the production of a sterol mix comprising cholesta-5,7,24(25)-trienol and zymosterol, wherein the percentage of cholesta-5,7,24(25)-trienol is about 75% or more based on the total amount of sterols produced by said yeast cell.

A yeast cell in which ERG5 and ERG6 are inactivated, wherein the ARE2 activity, e.g. activity of endogenous ARE2, has been reduced or abolished, said yeast cell being used for the production of a sterol mix comprising cholesta-5,7,24(25)-trienol and zymosterol, wherein the ratio between cholesta-5,7,24(25)-trienol and zymosterol present in the sterol mix is in the range of about 7 to about 1.

A yeast cell as above, wherein the yeast cell expresses a heterologous enzyme selected from EC 1.3.1.72 having sterol Δ24-reductase activity, preferably a heterologous enzyme that is active on lathosterol, zymosterol or trienol, wherein wherein the heterologous enzyme is originated from plant or vertebrate, more preferably originated from human, pig, dog, mouse, rat, horse or *Danio rerio*.

A yeast cell as above, wherein the ARE1 activity, e.g. activity of endogenous ARE1, has been reduced or abolished.

A yeast cell as above, wherein the ARE2 activity or ARE2 and ARE1 activity, e.g. activity of endogenous ARE2 or ARE2 and ARE1, has been abolished.

A process for decreasing the amount of zymosterol produced by a yeast cell by at least 4-times, said process comprising:

(a) providing a yeast cell, in which ERG5 and ERG6 are inactivated,
(b) abolishing or reducing the ARE2 activity within said yeast cell,
wherein the reduction is compared to a yeast cell wherein ARE2 is active, e.g.
wherein the endogenous ARE2 is active.

Use of a yeast cell as above for production of sterols, preferably for the production of vitamin D3 precursors, more preferably for the production of 7-DHC.

A process for the production of a sterol mix, preferably a vitamin D3-precursor, more preferably 7-DHC, in a yeast cell comprising:

(a) inactivation of ERG5 and ERG6,
(b) reducing or abolishing the activity of ARE2 or reducing or abolishing the activity of ARE1 and ARE2,
(c) expressing of a heterologous enzyme selected from EC 1.3.1.72 having sterol Δ24-reductase activity on lathosterol, zymosterol or trienol, preferably plant or vertebrate sterol Δ24-reductase, more preferably vertebrate sterol Δ24-reductase,
(d) cultivating said yeast cell under conditions suitable for sterol production;
wherein the amount of zymosterol present in the sterol mix is about 3% or less based on the total amount of sterols.

A process as above, wherein the ratio between 7-DHC and zymosterol present in the sterol mix is in the range of at least about 87 to about 2.

FIGURES

FIG. 1. Total sterol analysis (GC/MS) of knock-out strains e5e6 (panel A), a2e5e6 (panel B), and a1a2e5e6 (panel C), 1: cholesterol (added as internal standard, 10 μg per 10 OD units biomass), 2: zymosterol 3: cholesta-5,7,24(25)-trienol, 4: cholesta-7,24-dienol.

Figure 2:
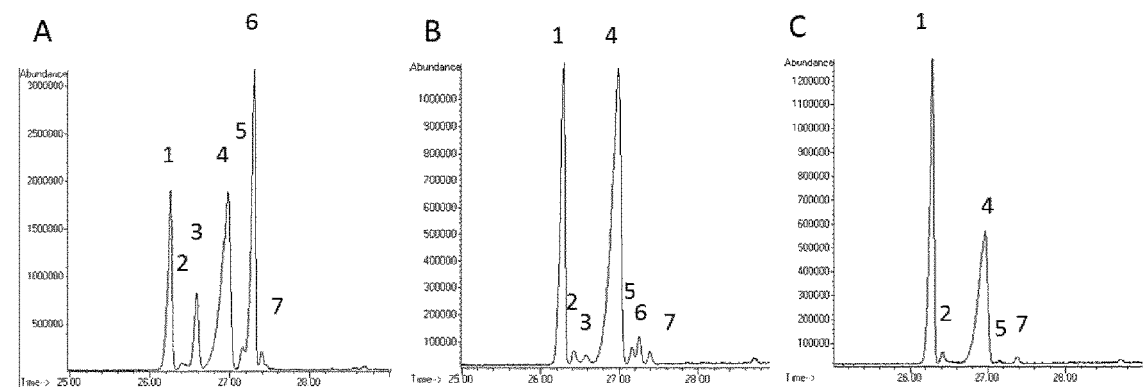

FIG. 2. Total sterol analysis (GC/MS) of strains e5e6::24R, a2e5e6::24R (panel A), a1a2e5e6::24R (panel B), and a1a2e5e6::24R (panel C); 1: cholesterol (added as internal standard, 10 μg per 10 OD units biomass), 2: cholesta-5,8-dienol 3: cholesta-8-enol, 4: 7-dehydrocholesterol, 5: cholesta-7-enol, 6: zymosterol, 7: cholesta-5,7,24-trienol.

Figure 3A:
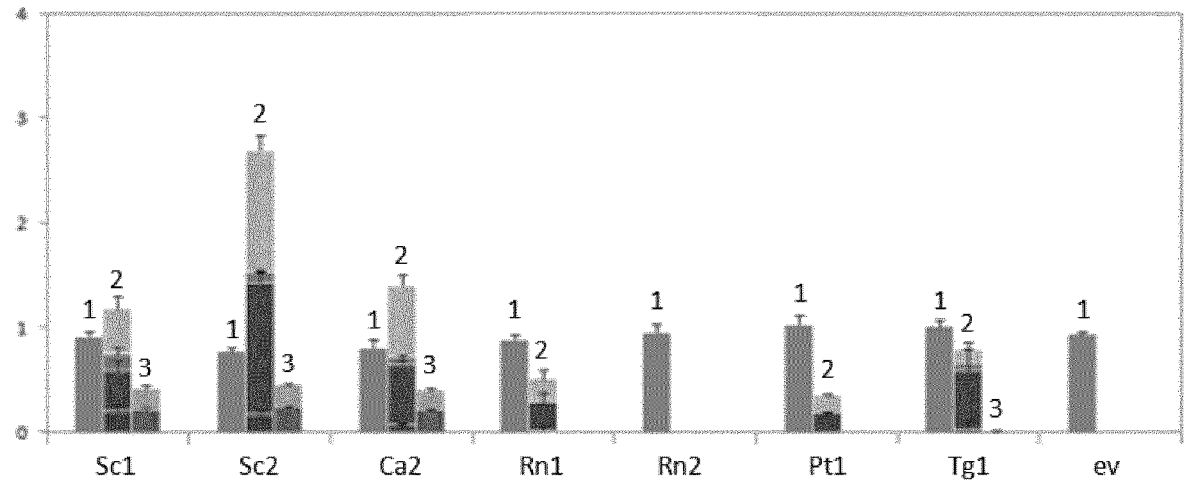
Figure 3B:
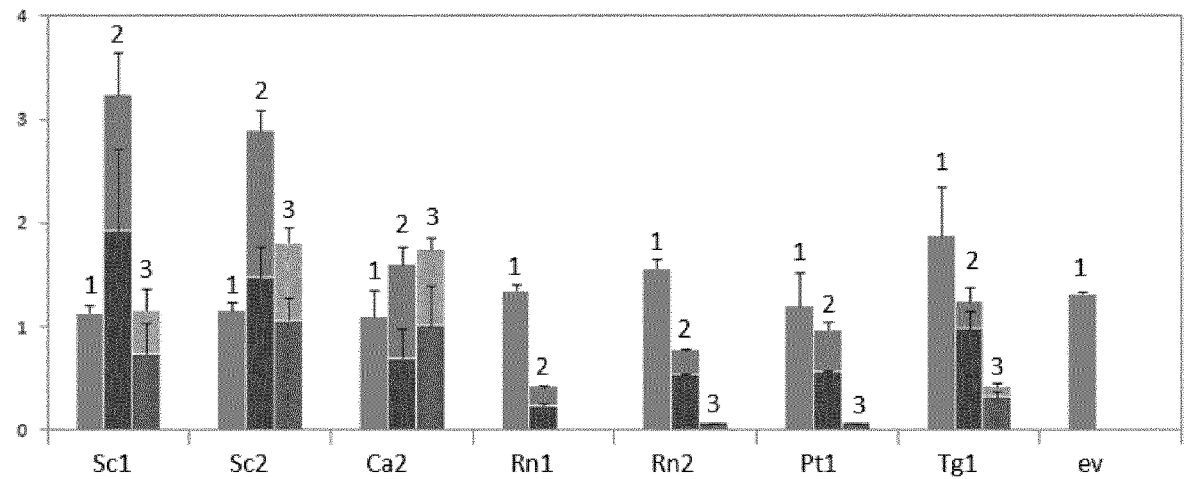
Figure 3C:
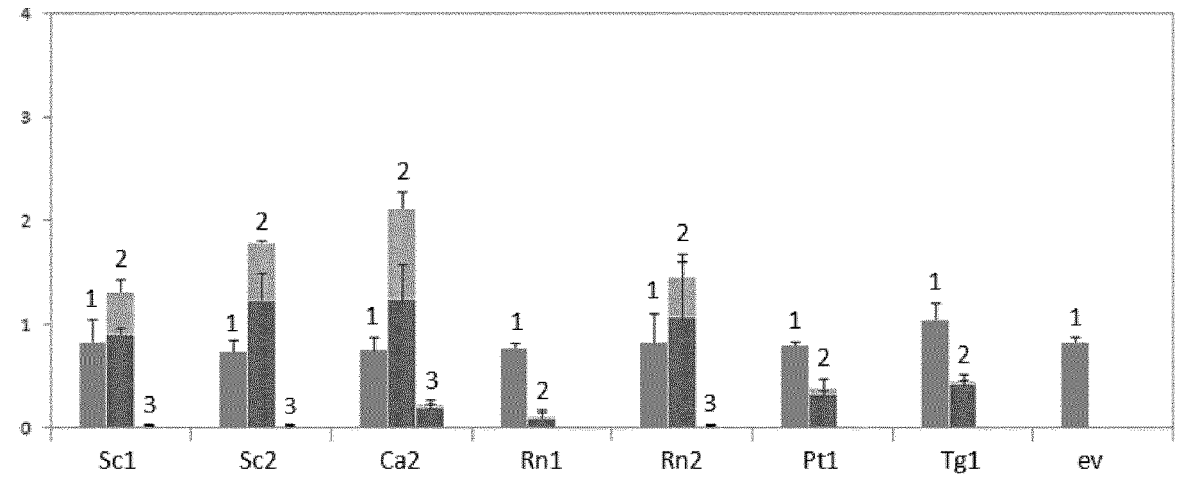

FIG. 3. Free sterol and sterol esters composition in acyltransferase expression strains given in $\mu g/OD_{600}$. HPLC-MS measurements of ergosterol (ERG), 7-Dehydrocholesterol (7-DHC), cholesterol (CLR) and zymosterol (ZYM). Mean values and standard deviations for ERG- and CLR-strains calculated from biological triplicates; for 7-DHC-strain from biological duplicates cultivated in parallel (except for Pt1*, Tg1*: independent cultivation). Samples of 200 $OD_{600}$ units were taken after 48 h acyltransferase expression in ergosterol producing strains (ERG-strains), with measurement of free ERG (column 1), ERG-esters (column 2) and ZYM-esters (column 3) is shown for the different sources of ARE (FIG. 3A). Within a column, the dark color shows ester 1, whereas the lighter color shows ester 2. Samples of 200 $OD_{600}$ units were taken after 65 h acyltransferase expression in 7-DHC producing strains (7-DHC-strains), with measurement of free 7-DHC (column 1), 7-DHC-esters (column 2) and ZYM-esters (column 3) is shown for the different sources of ARE (FIG. 3B). Within a column, the dark color shows ester 1, whereas the lighter color shows ester 2. Samples of 200 $OD_{600}$ units were taken after 65 h acyltransferase expression in cholesterol producing strains (CLR-strains), with measurement of free CLR (column 1), CLR-esters (column 2) and ZYM-esters (column 3) is shown for the different sources of ARE (FIG. 3C). Within a column, the dark color shows ester 1, whereas the lighter color shows ester 2.

Figure 4A:
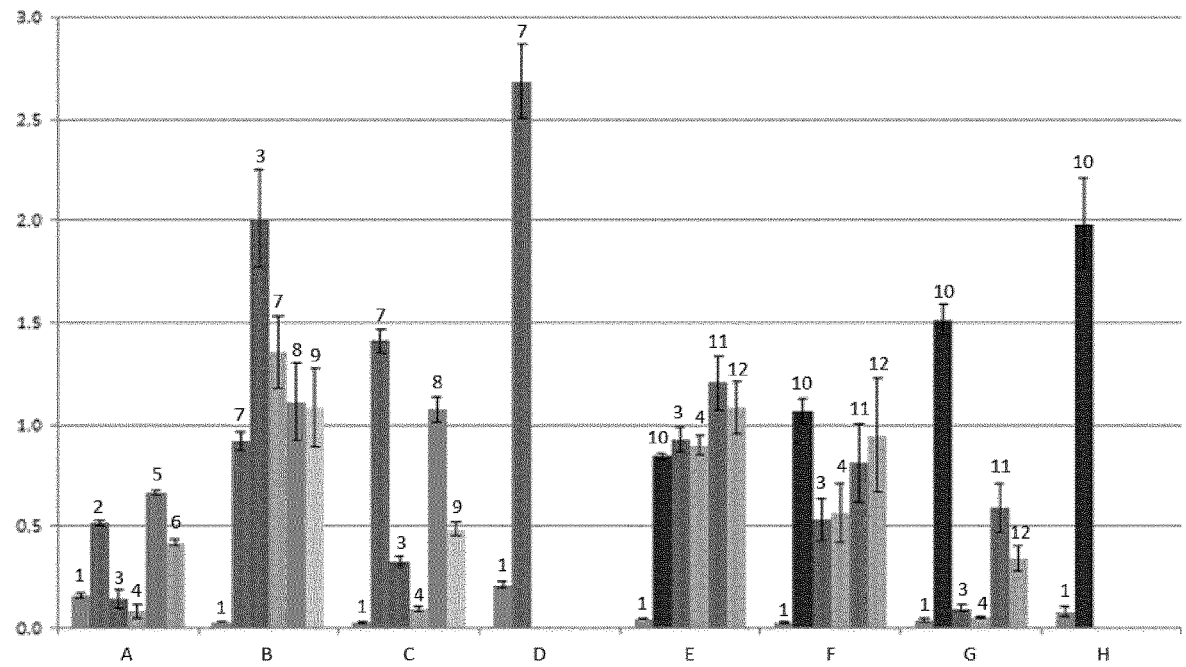
Figure 4B:
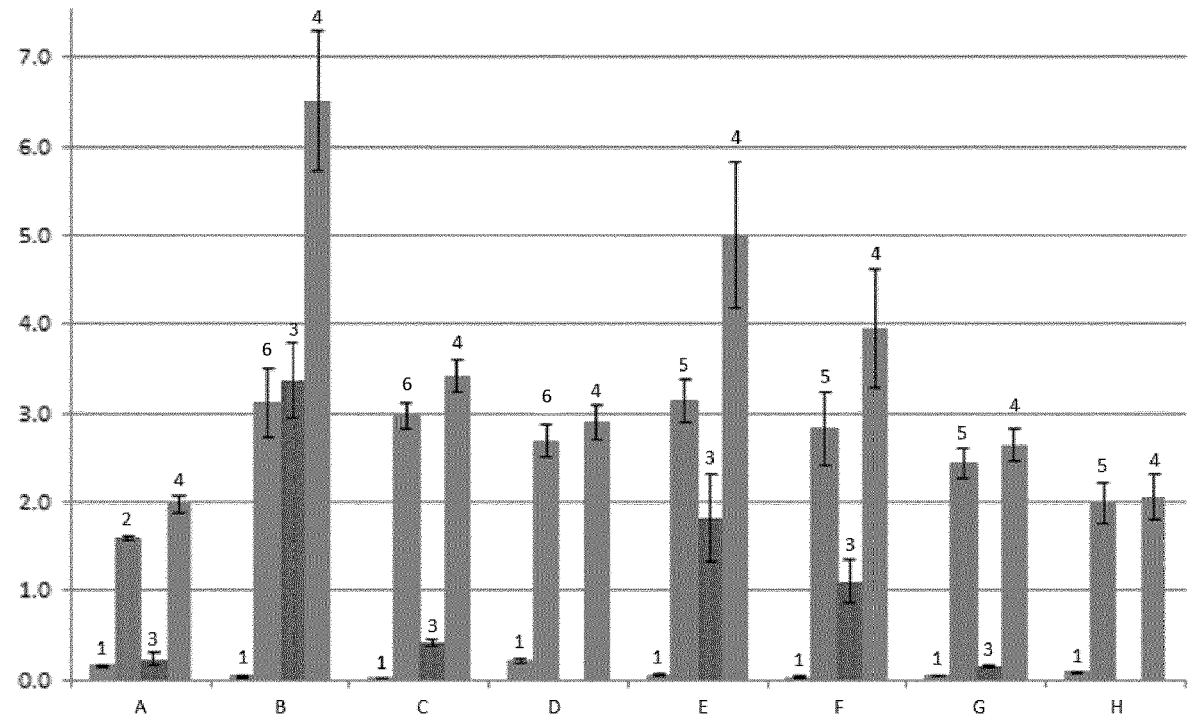

FIG. 4. HPLC analysis of ethanolic lipid extracts given in mg sterol/ml extract of CEN.PK2 strains (A) with different combinations of knock-outs, i.e. erg5/erg6 k.o. (B and E), are2/erg5/erg6 k.o. (C and G), are1/are2/erg5/erg6 k.o. (D and H), and are1/erg5/erg6 k.o. (F). Strains shown under (E), (F), (G) and (H) are further expressing 24-reductase gene. Strains were cultivated in YPD with 2% glucose for three days with three times glucose feeding (2%) in shake flasks with baffles. Data are from biological triplicates are given as different major sterol or steryl ester species, such as squalene (column 1), ergosterol (column 2), zymosterol ester (column 3 & 4), ergosterol ester (column 5 & 6), trienol (column 7), trienol ester (column 8 & 9), 7-DHC (column 10), 7-DHC ester (column 11 & 12), wherein the sterol esters shown in column 3, 5, 8, 11 are esterified with palmitoleic acid and the sterol esters shown in column 4, 6, 9, 12 are esterified with oleic acid (FIG. 4A). Data from biological triplicates given as sum of free and esterified sterols, such as squalene (column 1), ergosterol (column 2), zymosterol (column 3), total (column 4), 7-DHC (column 5), trienol (column 6) are shown in FIG. 4B.

Figure 5A:
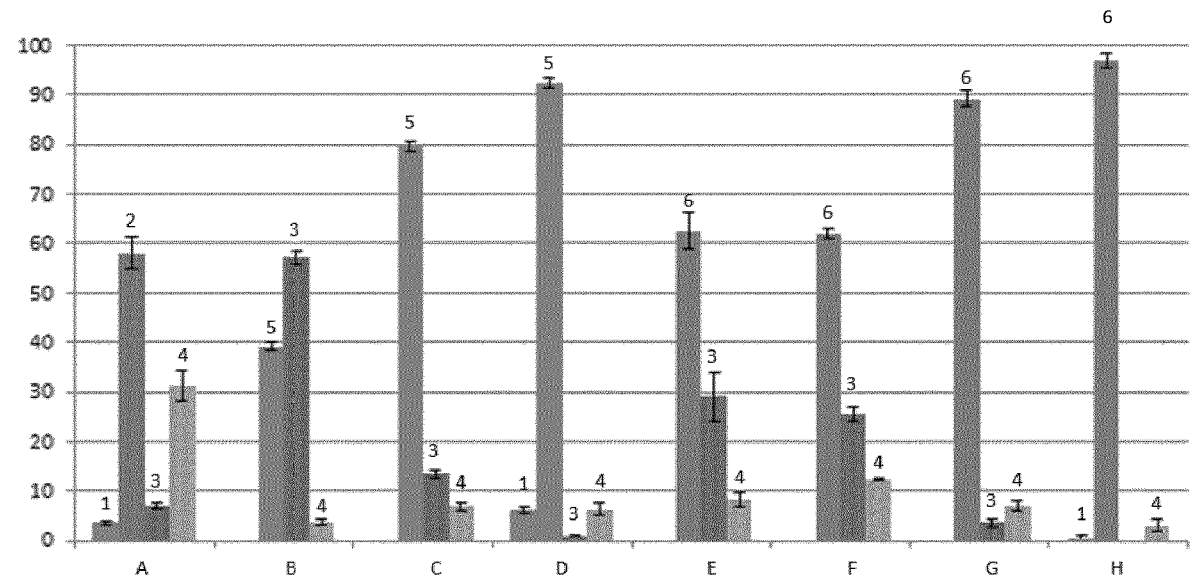
Figure 5B:
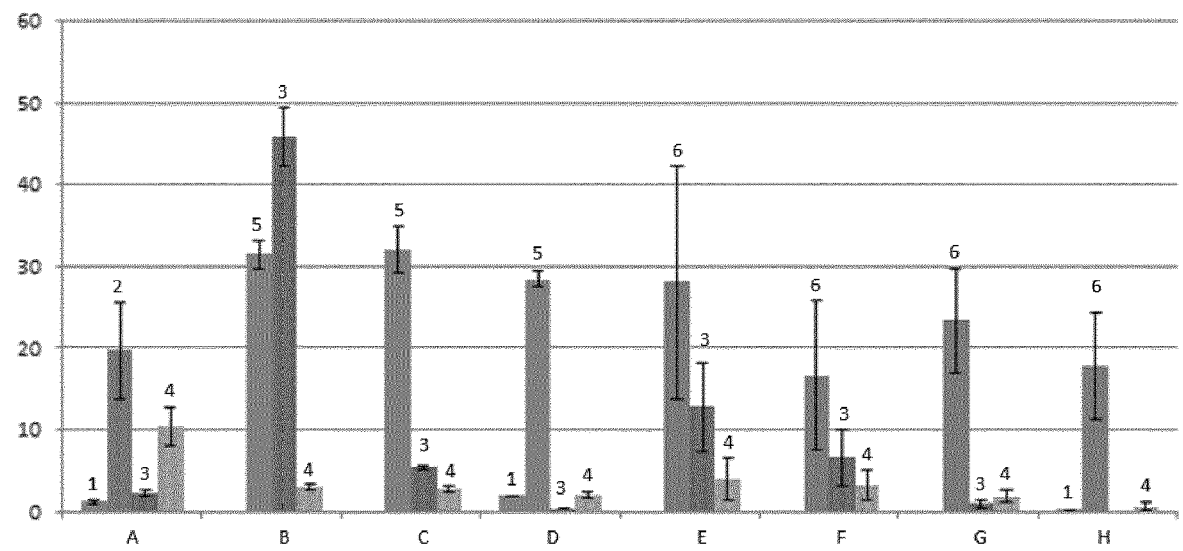

FIG. 5. GC/MS analysis of total sterols of CEN.PK2 strains (A) with different combinations of knock-outs, i.e. erg5/erg6 k.o. (B and E), are2/erg5/erg6 k.o. (C and G), are1/are2/erg5/erg6 k.o. (D and H), and are1/erg5/erg6 k.o. (F). Strains shown under (E), (F), (G), and (H) are further expressing 24-reductase gene. Extracts of these strains were used of the same biomass as for HPLC analysis. Data are from biological triplicates showing total sterols, such as squalene (column 1), ergosterol (column 2), zymosterol (column 3), other sterols (column 4), 7-DHC (column 5), trienol (column 6) either as percentage of total sterols (FIG. 5A) and as absolute amounts in μg per 10 OD units by normalization to the internal standard cholesterol (FIG. 5B).

The following examples are illustrative only and are not intended to limit the scope of the invention in any way.

EXAMPLES

Example 1: Construction of Knock-Out Strains Producing Cholesta-5,7,24-Trienol

A cholesta-5,7,24-trienol producing *Saccharomyces cerevisiae* strain (erg5 and erg6 knock-out, strain e5e6) with are1 and are2 knock-out (strain a1a2e5e6, see Table 1) and a strain with only are2 knock-out (strain a2e5e6) or are1 knock-out (strain 20B) were isolated by tetrad dissection after sporulation of the diploid strain COS24. The diploid strain COS24 was gained by crossing of the two strains COS23 (are1 are2 knock-out; a1a2) and BP5 (erg5 erg6 knock-out; e5e6), which were constructed by knock-out of the specified genes (see Table 1) with disruption cassettes carrying an auxotrophy marker, or in case of Are2 with a disruption cassette carrying an antibiotic resistance gene. Interesting strains comprising ARE2 or ARE1/2 k.o. were identified by growth characteristics on marker plates. Genomic manipulations were confirmed by cPCR.

Disruption cassettes were amplified by PCR using primers composed of approximately 40 bp at the 5'-end of the primer that are homologous to the up-or downstream region of the gene which is meant to be deleted and 20 bp at the 3'-end of the primer that anneal to the selectable marker gene which is meant to be introduced (Longtine, 1998; Lorenz, 1995). In case of are1 knockout, the disruption cassette flanking regions matched the N- and C-terminal part of the ARE1 gene and the disruption cassette carried a TEF promoter and terminator for expression of the HIS3 gene. For the other three knockouts the promotors of the knocked out genes were used for marker expression. For a summary of the primers for the generation of the disruption cassettes and a list of the corresponding template vectors see Table 7 and Table 2.

The disruption cassettes were transformed into *Saccharomyces cerevisiae* with the method described below and homologous recombinants were identified by marker prototrophy or antibiotic resistance.

Prior to transformation, all strains were cultivated in YPD at 30° C. in 10 or 50 mL pre-culture overnight. The main culture was inoculated to an $OD_{600}$ of 0.05 in 50 mL grown over night until an $OD_{600}$ of 1.5-2 units was reached. Transformation of plasmids was performed according to high efficiency LiAc/SS carrier DNA/PEG protocol described by Gietz and Woods (2002). Briefly, cells were harvested at 3000×g for 5 min, washed with 25 mL of sterile water at 3000×g, 5 min and resuspended in 1 mL sterile water. Cells were transferred to a 1.5 mL reaction tube, again centrifuged at 500×g, 1 min, supernatant removed and filled up to final volume of 1 mL with sterile water. Aliquots of 100 μL (≈108 cells) were centrifuged at 500×g, 1 min and supernatant removed. The transformation mix containing 240 µL of PEG 3500 (50%), 36 µL of 1 MLiAc, 50 µL of boiled SS-carrier DNA and 34 µL of 1-2 µg plasmid DNA or linear disruption cassettes were added to the cell pellets, vigorously mixed and incubated at 42° C. for 40 min. After the transformation event, samples were regenerated in 1 mL of YPD for 3.5 h. The suspension was centrifuged for 5 min at 500×g to gently spin down the cells. Cells were plated out on selection plates.

Correct knock-outs were verified in several different colony PCR setups. The ERG5, ERG6, ARE1 and ARE2 genes were replaced by LEU2, TRP1, HIS3 and the loxP-kanMX-loxP disruption cassettes, respectively, as described by Güldener et al. (1996) to finally yield the are1are2erg5erg6 quadruple knock-out strain (strain a1a2e5e6).

TABLE 1 genotype and mating type of strains used for the present invention. Strain e5e6 carries a k.o. of ERG5 and ERG6, strain a2e5e6 carries k.o. of ERG5, ERG6 and ARE2, strain a1a2e5e6 carries a k.o. of ERG5, ERG6, ARE1 and ARE2.

| Strain | Genotype | Mating type |
|---|---|---|
| BP1 (e5) | CEN.PK2 MATα his 3 ura3 MAL2 SUC2 erg5::LEU2 | alpha |
| BP10 (e6) | CEN.PK2 MATα his 3 ura3 MAL2 SUC2 erg6::TRP1 | a |
| BP5 (e5e6) | CEN.PK2 MATα his 3 ura3 MAL2 SUC2erg5::LEU2, erg6::TRP1 | alpha |
| BP24 (E5e5E6e6) | CEN.PK2 ura3/ura3 his3/his3 MAL2/Mal2 SUC2/SUC2 ERG5/erg5::LEU2 ERG6/erg6::TRP1 | diploid |
| BP8 (A1a1A2a2E5e5E6e6) | CEN.PK2 ura3/ura3 MAL2/Mal2 SUC2/SUC2 ARE1/are1::HIS3 ARE2/are2::kanMX ERG5/erg5::LEU2 ERG6/erg6::TRP1 | diploid |
| DSM2 | CEN.PK2 ura3/ura3 MAL2/MAL2 SUC2/SUC2 ARE1/are1::HIS3 ARE2/are2::kanMX ERG5/erg5::LEU2 erg6::24DHCR-HPH/erg6::TRP1 | diploid |
| 2B (a2e5e6) | CEN.PK2 MATα his3 ura3 MAL2 SUC2 are2::kanMX erg5::LEU2 erg6::TRP1 | a |
| 20B (a1e5e6) | CEN.PK2 MATα ura3 MAL2 SUC2 are1::SkHIS3 erg5::LEU2 erg6::TRP1 | n.d. |
| 14C (a1a2e5e6) | CEN.PK2 MATα ura3 MAL2 SUC2 are1::HIS3 are2::kanMX erg5::LEU2 erg6::TRP1 | alpha |
| e5e6::24R | CEN.PK2 MATα his3 ura3 trp1 MAL2 SUC2 erg5::LEU2, erg6::24DHCR-HPH | a |
| 4D (a2e5e6: :24R) | CEN.PK2 MATα his3 ura3 MAL2 SUC2 are2::TRP1, erg5::LEU2, erg6::24DHCR-HPH | |
| 10A (a1a2e5e6: :24R) | CEN.PK2 MATα ura3 MAL2 SUC2 are1:: HIS3 are2::TRP1, erg5::LEU2, erg6::24-DHCR-HPH | |
| COS6 (e5e6::24R) | CEN.PK2 MAT☐ his 3 ura3 MAL2 SUC2 erg5::LEU2 erg6::24DHCR-HPH | |
| COS23 (a1a2) | CEN.PK2 MATα ura3 leu2 trp1 MAL2 SUC2 are1::SkHIS3 are2::kanMX | a |

TABLE 1-continued genotype and mating type of strains used for the present invention. Strain e5e6 carries a k.o. of ERG5 and ERG6, strain a2e5e6 carries k.o. of ERG5, ERG6 and ARE2, strain a1a2e5e6 carries a k.o. of ERG5, ERG6, ARE1 and ARE2.

| Strain | Genotype | Mating type |
|---|---|---|
| COS4 (a1a2) | CEN.PK2 MATα ura3 leu2 trp1 MAL2 SUC2 are1::SkHIS3 are2::TRP1 | a |
| COS 24 (A1a1A2a2E5e5E6e6) | CEN.PK2 ura3/ura3 MAL2/MAL2 SUC2/SUC2 ARE1/are1::SkHIS3 ARE2/are2::kanMX ERG5/erg5::LEU2 ERG6/erg6::TRP1 | |
| COS3 (A1a1A2a2E5e5E6e6::24R) | CEN.PK2 ura3/ura3 MAL2/Mal2 SUC2/SUC2 ARE1/are1::SkHIS3 ARE2/are2::TRP1 ERG5/erg5::LEU2 ERG6/erg6::24-DHCR-HPH | diploid |
| COS9 (a1a2e5e6::24R) | CEN.PK2 MAT☐ ura3 MAL2 SUC2 are1::SkHIS3 are2::TRP1 erg5::LEU2 erg6::24-DHCR-HPH | alpha |
| COS7 (a1e5e6::24R) | CEN.PK2 MAT☐ ura3 MAL2 SUC2 are1::SkHIS3 erg5::LEU2 erg6::24-DHCR-HPH | alpha |
| COS8 (a2e5e6::24R) | CEN.PK2 MAT☐ ura3 MAL2 SUC2 are2::TRP1 erg5::LEU2 erg6::24-DHCR-HPH | a |

"N.d." means "not determined" (for more explanation see text).

TABLE 2 plasmids used as templates for markers in disruption cassettes (for more explanation see text).

| Plasmid | Characteristic |
|---|---|
| pRS315 | LEU2-f1 ori (NaeI)-T7 promoter-lacT/MCS-T3 promoter-pMB1 ori-bla-CEN6-ARSH4 |
| pFA6a | TRP1 TRP1-pBR322 ori-T7 promoter-lacT/MCS-ampR-CEN6 |
| pUG6 | ampR-loxP-kanMX-TEF2 promoter |
| pFA6a-His3MX6 | SkHIS 3 |

Example 2: GC/MS Analysis or Strains Wherein ARE2 or ARE1/2 have been Knocked-Out Total sterols of knock-out strains e5e6 (control), a2e5e6 and a1a2e5e6 were analyzed by GC/MS (Table 3).

Strains were cultivated in shake flasks in YPD media for 48 h. 10 $OD_{600}$ units of biomass were saponified with KOH/MeOH and extracted with n-heptane.

Absolute amounts [µg] were calculated from peak area of cholesterol peak. As internal standard, 10 µg of cholesterol were added to 10 OD units. With regards to zymosterol, the amount varied from 17.2 µg (e5e6) to 2.5 µg (strain a2e5e6) to 0.41 µg (strain a1a2e5e6). For Cholesta-5,7,24(25)-trienol, the amount varied from 18 µg (e5e6) to 20 µg (a2e5e6) to 19 µg (a1a2e5e6).

TABLE 3

Total sterol analysis of strains e5e6, a2e5e6 and a1a2e5e6.
For more explanation see text.

| | % of total sterols | | |
|---|---|---|---|
| | e5e6 | a2e5e6 | a1a2e5e6 |
| Cholesta-5,8,24(25)-trienol | 1.0 | 2.0 | 2-0 |
| Zymosterol | 43.5 | 9.5 | 2.0 |
| Cholesta-5,7,24(25)-trienol | 47.5 | 76.0 | 86.5 |
| Cholesta-7,24(25)-dienol | 7.0 | 7.0 | 5.0 |

Knockout of ARE2 leads to a drastic reduction of zymosterol content (in the range of 4-times) based on total sterols, an additional knockout of ARE1 further reduced zymosterol to 2%. Trienol content increased up to 76% for are2 knockout and further to around 86% for double knockout.

Example 3: Construction of 7-DHC Producing Strains with Single or Double Knock-Out of ARE1 and ARE2

For the construction of a 7-DHC producing *S. cerevisiae* strain without acyltransferase activity first a CEN.PK2 MATα erg5 knock-out and a CEN.PK2 MATα erg6 knock-out strain were constructed with the disruption cassettes described in Example 1. These two strains were crossed to give a diploid ERG5/erg5::LEU5 ERG6/erg6::TRP1 strain, into which the disruption cassettes for ARE1 and ARE2 knock-out were transformed. These transformations yielded the diploid strain ARE1/are1::HIS3 ARE2/are2::kanMX ERG5/erg5::LEU2 ERG6/erg6::TRP1. Into this strain a disruption cassette was transformed that contained the gene for a sterol 24-reductase from *Danio rerio* flanked by a TDH3 promoter and a PGK1 terminator in combination with a gene for hygromycin resistance with TEF1 promoter and terminator (24DHCR-HPH). The disruption cassette was integrated in the ERG6 locus, thereby a CEN.PK2 ARE1/are1::HIS3 ARE2/are2::kanMX ERG5/erg5::LEU2 erg6::24-DHCR-HPH/erg6::TRP1 strain was obtained. After sporulation of this strain and a tetrad dissection an erg5::LEU5 erg6::24DHCR-HPH knock-out strain was isolated. This strain was mated with an are1::HIS3 are2::TRP1 knock-out strain (constructed with disruption cassettes described in Example 9). The resulting diploid strain was sporulated and after a tetrad dissection finally a CEN.PK2 are1::SkHis3 are2::kanMX erg5::LEU5 erg6::24DHC-HPH quadruple knock-out strain expressing a sterol 24-reductase was obtained, which produced 7-DHC as the main sterol. Moreover two strains with only ARE1 (COS7) or ARE2 (COS8) knockout were isolated.

Example 4: GC/MS Analysis of Strains a2e5e6::24R and a1a2e5e6::24R

Total sterols of knock-out strains e5e6::24R (control), a2e5e6::24R and a1a2e5e6::R24 were analyzed by GC/MS (Table 4).

Strains were cultivated in shake flasks in YPD media for 48 h. 10 $OD_{600}$ units of biomass were saponified with KOH/MeOH and extracted with n-heptane. Absolute amounts [μg] were calculated from peak area of cholesterol peak. As internal standard, 10 μg of cholesterol were added to 10 OD units. With regards to zymosterol, the amount varied from 17.2 μg (e5e6::24R) to 2.5 μg (a2e5e6::24R) to 0.41 μg (a1a2e5e6::24R).

TABLE 4

Total sterol analysis of strains e5e6::24R, a2e5e6::24R and a1a2e5e6::24R. For more explanation see text.

| | % of total sterols | | |
|---|---|---|---|
| | e5e6::24R | a2e5e6::24R | a1a2e5e6::24R |
| Cholesta-5,8-dienol | 3 | 3 | 5 |
| Cholesta-8-enol | 10 | 2 | n.d. |
| 7-DHC | 44.5 | 87 | 92 |
| Cholesta-7-enol | 4 | 2 | n.d. |
| Zymosterol | 33.5 | 2 | n.d. |
| Cholesta-5,7,24-trienol | 3 | 2 | 2 |

The term "n.d." means "not detectable".

From the amount of total sterols obtained with strain e5e6::24R around 45% is 7-DHC and 34% of sterols are zymosterol. The amount of 7-DHC was dramatically increased to 87% of the total sterols produced by a strain that possessed a knock-out in ARE2; it was further increased to over 90% in strains that possessed a double k.o. of ARE1/2. Absolute amounts of 7-DHC decreased from 20 μg per 10 OD units to 9 μg in strain a1a2e5e6::24R under the given conditions, but the by-product formation was further decreased as no zymosterol was detected any more.

Example 5: Construction of a Cholesterol Producing *S. cerevisiae* Strain without Acyltransferase Activity To generate a new *S. cerevisiae* CEN.PK strain which stably produces cholesterol instead of ergosterol, dehydrocholesterol reductase DHCR7 originating from *Danio rerio* (Zebrafish) was integrated into the 7-DHC producing are1are2 knock-out strain 10A (a1a2e5e6::24R, see Example 6). DHC7 saturates 7-DHC at its double bond position C-7 resulting in the final product cholesterol.

DHCR7 gene was amplified by PCR from vector 056662pScript along with Bam HI and Eco RI restriction sites and an additional 5' Kozak consensus sequence "AAAA" for *S. cerevisiae* using primers DHCR7-FW and DHCR7-RV (Table 13). This PCR-product was then used as an insert for sticky-end ligation with the vector backbone of p426GPD_ARE2 after Bam HI and Eco RI double digestion. The created vector p426GPD_DHCR7 now contained the DHCR7 gene flanked by the strong pTDH3 and the terminator of iso-1-cytochrome tCYC1. This cassette capable of introducing DHCR7 overexpression was amplified by PCR, using primers HR-TDH3-FW and CYC1t-HR-RV adding the 5' and 3' homologous ERG5 regions. All primers are shown in Table 7.

The DHC7 disruption cassette was transformed into strain 10A (a1a2e5e6::24R). As only cholesterol producing strains can stand natamycin, the transformed cells were plated on 40-60 μM natamycin, where only cells with functional 7-DHC reductase expression could survive. Colony PCR results confirmed correct integration of the disruption cassette into the ERG5 locus. GC-MS results showed, that the resulting yeast strain BA-C produced >99% cholesterol in total sterols.

Example 6: Transformation and Isolation of Plasmid DNA Carrying Synthetic Genes for Sterol-O-Acyltransferases (HATs)

Synthetic genes coding for five different HATs from four organisms were ordered at DNA2.0. All gene constructs were optimized for the expression in S. cerevisiae and delivered in a pJ201 vector (Table 5).

TABLE 5

Selection of HATs including the designation of the vectors (based on DNA 2.0 vector pJ201), detailed list of proteins, source organism and NCBI accession numbers.

| Vector | Sterol-o-acyltransferase | Organism | NCBI Accession number |
|---|---|---|---|
| pHYD-0120 | sterol O-acyltransferase 1 | Pan troglodytes (Pt1) | XP_514030 |
| pHYD-0121 | sterol O-acyltransferase 2 | Rattus norvegicus (Rn2) | EDL86862.1 |
| pHYD-0122 | sterol O-acyltransferase 1, isoform CRA_a | Rattus norvegicus (Rn1) | EDM09484.1 |
| pHYD-0123 | hypothetical protein CaO19.2248 | Candida albicans SC5314 (Ca2) | XP_714838 |
| pHYD-0124 | sterol O-acyltransferase, putative | Toxoplasma gondii VEG (Tg1) | EEE27951.1 |

The plasmids pHYD-0120-0124 and the p426GPD vector (Mumberg, 1995) were transformed into electro-competent E. coli TOP10F' cells, regenerated in SOC medium for 1 h at 37° C. and plated on LB-Kanamycin (50 µg/mL) agar plates for pHYD transformations and on LB-Ampicillin (100 µg/mL) for p426GPD transformation. The plates were incubated at 37° C. overnight. Media composition is given in Table 6.

TABLE 6

Composition of cultivation media. For liquid media, agar is omitted.

| Medium | Composition |
|---|---|
| LB | 10 g/L tryptone, 5 g/L yeast extract, 5 g/L NaCl, 20 g/L agar |
| SOC | 20 g/L bacto tryptone, 0.58 g/L NaCl, 5 g/L bacto yeast extract, 2 g/L MgCl$_2$, 0.16 g/L KC, 2.46 g/L MgSO4, 3.46 g/L dextrose |

Single colonies from the transformation plates were streaked on LB-Kanamycin (50 µg/mL) agar plates and grown overnight at 37° C. Plasmids were isolated from cell material taken from the agar plates with the Gene Jet Plasmid Miniprep Kit (Fermentas Thermo Fisher Scientific Inc.) according to the manual.

Example 7: Amplification of the ARE1 and ARE2 Gene from Chromosomal DNA of Saccharomyces cerevisiae CEN.PK2 and Cloning into Vector pJet1.2

Genomic DNA isolation was done according to the "Bust n' Grab" method (Harju, 2004). 1.5 ml of an overnight culture (OD$_{600}$ 12) of EUROSCARF strain Saccharomyces cerevisiae CEN.PK2-1D (MATα, ura3-52, trp1-289, leu2-3_112, his301, MAL2-8c, SUC2) were transferred into a microfuge tube and pelleted at 13,000×g for 5 min. The pellet was resuspended in 200 µL of lysis buffer (2% Triton X-100,1% SDS, 100 mM NaCl, 10 mM Tris-HCl, pH 8.0, 1 mM EDTA, pH 8.0) and placed in a −80° C. freezer until completely frozen. The mixture was quickly thawed in a thermomixer at 95° C. This procedure was repeated twice before vortexing the sample for 30 s. After adding 200 µL of chloroform, the tubes were vortexed for 2 min and centrifuged for 3 min at room temperature and maximum speed. For DNA precipitation, the upper aqueous phase was transferred to a microcentrifuge tube containing 400 µL of ice-cold 100% ethanol and mixed by inversion. To increase the yield, samples were incubated at −20° C. for 5-10 min and centrifuged for 5 min at 16,100×g. The supernatant was removed and the pellet was washed with 0.5 mL 70% ice-cold ethanol. After centrifugation at 16,000×g for 5 min the supernatant was removed with a micropipette and the pellet was dried in an incubator at 30° C. before dissolving it in 20 µL of TE buffer (10 mM Tris-HCl, 1 mM EDTA, pH 8).

To amplify ARE1 and ARE2, genomic DNA of CEN.PK2 was used as template in a two-step PCR. The primers provided overhangs with restrictions sites (BamHI and EcoRI) for cloning (see Table 7).

TABLE 7

Primers for the amplification/cloning of ARE1 and ARE2 (for more details see text).

| Primer | Sequence (5' to 3') | SEQ ID NO |
|---|---|---|
| are1-fw | CTATATGGATCCAAAATGACGGAGACT AAGGATTTGTTGC | 1 |
| are1-rv | GACTGCGAATTCTCATAAGGTCAGGTA CAACGTCATAATG | 2 |
| are1_c1332a_rv | GTGGCGGGTATCCAGCCGCCGAAG | 3 |
| are1_c1332a_fw | CTTCGGCGGCTGGATACCCGCCAC | 4 |
| are2-fw | CTATATGGATCCAAAATGGACAAGAAG AAGGATCTACTGG | 5 |
| are2-rv | GACTGCGAATTCTTAGAATGTCAAGTA CAACGTACACATG | 6 |
| E6Trp1 | CATAATTTAAAAAAACAAGAATAAAAT AATAATATAGTAGGCAGCATAAGATGT CTGTTATTAATTTCACAGG | 7 |
| E6Trp2 | ATAGGTATATATCGTGCGCTTTATTTG AATCTTATTGATCTAGTGAATTTCTAT TTCTTAGCATTTTTGACG | 8 |
| E5Leu1 | AAAACATCACATTTTGCTATTCCAATA GACAATAAATACCTTTTAACAAAATGT CTGCCCCTAAGAAGATC | 9 |
| E5Leu2 | TAATGAAGTAAATATGATTTATTGTCT GGACAAAGTTCTGTTTTTCCCCATTAA GCAAGGATTTTCTTAACTTC | 10 |
| FW_A2lox | CTATAAAGATTTAATAGCTCCACAGAA CAGTTGCAGGATGCCGCATAGGCCACT AGTGGATCTG | 11 |
| RV_A2lox | CTATAAAGATTTAATAGCTCCACAGAA CAGTTGCAGGATGCCGCATAGGCCACT AGTGGATCTG | 12 |
| ARE3His3_fw | ATGACGGAGACTAAGGATTTGTTGCAA GACGAAGAGTTTCTTAAAGCTTGCCTC GTCCCCGCC | 13 |
| ARE3His3_rv | TCATAAGGTCAGGTACAACGTCATAAT GATACTGGGCCCTGAACTGGATGGCGG CGTTAGTATCG | 14 |
| DHCR7-FW | GTTGTTGGATCCAAAAATGATGGCTTC AGATAGAGTTAGAAAAGAC | 15 |
| DHCR7-RV | CAACAAGAATTCTCATCAGAAAATATT TGGCAATAATCTATAAG | 16 |

TABLE 7-continued

Primers for the amplification/cloning of ARE1 and ARE2 (for more details see text).

| Primer | Sequence (5' to 3') | SEQ ID NO |
|---|---|---|
| HR-TDH3-FW | AAAACATCACATTTTGCTATTCCAATAGACAATAAATACCTTTTAACAAAAGTTTATCATTATCAATACTCGCCATTTCAAAGAATACG | 17 |
| CYC1t-HR-RV | TAATGAAGTAAATATGATTTATTGTCTGGACAAAGTTCTGTTTTTCCCCAGGCCGCAAATTAAAGCCTTCGAG | 18 |
| 120FLAGfw | GCGGGATCCATGGACTACAAAGACGATGACGATAAAGTCGGAGAGGAAAAGATGTCCCTGAC | 19 |
| 120FLAGrev | GCGGAATTCTCAGAAAACGTAACGACAAGTCCATGATCTAGGCCTAACGTAATCCAGAAAGG | 20 |
| 121FLAGfw | GCGGGATCCATGGACTACAAAGACGATGACGATAAAGAACCAAAAGCTCCACAATTACGTCG | 21 |
| 121FLAGrev | GCGGAATTCTCAAGGATGACAACTCCAGGATCTAGGTGTTACAAGTTCCCAAAATGTTGGTTGTGGTAATG | 22 |
| 122FLAGfw | GCGGGATCCATGGACTACAAAGACGATGACGATAAAGGATCCAAAATGGTAGGCGAGGAAATG | 23 |
| 122FLAGrev | GCGGAATTCTCAAAACACATATCTACAAGTCCATGTACGTGGTCTGACGTAATCAAGGAAAGTAGGGTTTTCAATGG | 24 |
| 123FLAGfw | GCGGGATCCATGGACTACAAAGACGATGACGATAAAGGCAGAACTAACACTTCTGATCAGC | 25 |
| 123FLAGrev | GCGGAATTCTCAAAAGACCAGGTACAGAGTACAGATAATGGAAGGGCCAGAGATGAAACCGAACCAACAAATGATGTTACC | 26 |
| 124FLAGfw | GCGGGATCCATGGACTACAAAGACGATGACGATAAATTAGATGATCCTTTGTCTAAAACTAG | 27 |
| 124FLAGrev | GCGGAATTCTCTCAAAACAATCTTAAAGGTTGATGATCGGCATGAGCATTGTAAAAGTGTATTTGTGCCC | 28 |
| ScARE1FLAGfwd | GCGGGATCCAAAATGGACTACAAAGCGATGACGATAAAACGGAGACTAAGGATTTGTTG | 29 |
| ScARE1FLAGrev | GCTGAATTCTCATAAGGTCAGGTACAACGTCATAATGATACTGGGCCCTGAACAGACAC | 30 |
| ARE2FLAGfwd | GCGGGATCCATGGACTACAAAGACGATGACGATAAAGACAAGAAGAAGGATCTACTGGAG | 31 |
| ARE2FLAGrev | GCGGAATTCTTAGAATGTCAAGTACAACGTACACATGACACTTGGTCCCATGCAGATACC | 32 |
| p426GPD_URAfw | AACACTACATATGCGTATATATACCAATCTAAG | 33 |
| p426GPD_URArv | GGTGGTGCGGCCGCCACAGATGCGTAAGGAGAAAATACC | 34 |
| NdeI TEFp_fw | GGTGGTCATATGAGCTTGCCTCGTCCCCG | 35 |
| NotI TEFt_rv | GGTGGTGCGGCCGCGGATGGCGGCGTTAGTATCG | 36 |
| Kozak-FLAG | CGCGGATCCGCGAAAATGGACTACAAAGACGATGACGATA | 37 |

PCR was carried out under following conditions: 50 μL total volume, 200 μM of each dNTP, 0.5 μM of each primer, approximately 200 ng of genomic DNA from S. cerevisiae CEN.PK2-1D, 0.03 U/μL Phusion Hot Start Polymerase in according buffer (Finnzymes Thermo Fisher Scientific Inc.). Cycling conditions were as follows: 98° C. for 1 min; 5 cycles of 98° C. for 10 s, 67.8° C. for 50 s, 72° C. for 58 s; 30 cycles of 98° C. for 10 s, 78° C. for 50 s, 72° C. for 59 s; 72° C. for 10 min, finally kept at 4° C.

Amplified DNA was purified by a preparative gel (Wizard SV Gel Slice and PCR Product Preparation by Promega) and cloned into pJet1.2 vector with the Clone Jet™ PCR Cloning Kit (Fermentas Thermo Fisher Scientific Inc.) according to the supplier's manual to get vector pJet1.2_ARE1 or pJet1.2_ARE2. Vectors pJet1.2_ARE1 and pJet1.2_ARE2 were transformed into E. coli TOP10F'. Cell material from an overnight cultivated streak out from a single transformant was used for plasmid isolation with Fermentas GeneJet Plasmid Miniprep Kit (Fermentas Thermo Fisher Scientific Inc.) according to the supplier's manual. The correct integration of ARE1 or ARE2 in pJET1.2 was checked by Sanger sequencing.

Example 8: Cloning of ARE1 and ARE2 Gene into Vector p426GPD

The ARE1 sequence from CEN.PK2 contains a BamHI restriction site, which was removed by mutation. Therefore, the ARE1 gene was amplified in two fragments with the primers indicated in Table 7. Primer are1_c1332a_fw and are1_c1332a_rv contained the intended mutation C1332A. For amplification of fragment 1 primer set are1_fw and are1_c1332a_rv was used, for amplification of fragment 2 primer set are1_c1332a_fw and are1_rv was used. The PCR mixture contained in 50 μL total volume 200 μM of each dNTP, 0.2 μM of each primer, 13 ng of pJET1.2_ARE1, 0.02 U/μL Phusion Polymerase in according buffer (Finnzymes Thermo Fisher Scientific Inc.). The PCR program used was: 98° C. for 30 s; 30 cycles of 98° C. for 10 s, 60° C. for 30 s, 72° C. for 60 s; 72° C. for 7 min, finally kept at 4° C. The two fragments were gel purified and merged in an overlap extension PCR reconstituting the whole ARE1 gene with mutated BamHI restriction site. The reaction mixture for the overlap extension PCR contained in 50 μL total volume 200 μM of each dNTP, 10 ng of fragment 1, 7 ng of fragment 2, 0.02 U/μL Phusion Polymerase in appropriate buffer (Finnzymes Thermo Fisher Scientific Inc.). The PCR program used was: 98° C. for 30 s; 15 cycles of 98° C. for 10 s, 60° C. for 20 s, 72° C. for 90 s; 72° C. for 7 min, finally kept at 4° C. The PCR product (mutated ARE1 gene flanked by BamHI and EcoRI restriction sites) was gel purified and used as insert for further cloning steps.

For insert preparation for cloning of mutated ARE1 and ARE2 into p426GPD the amplified ARE1 gene (see above) or pJet1.2_ARE2 and p426GPD were restricted with BamHI and EcoRI (Fermentas Thermo Fisher Scientific Inc.). The ARE2 insert and p426GPD vector backbone were purified by a preparative gel, the ARE1 insert was purified via the GeneJET PCR Purification Kit (Fermentas Thermo Fisher Scientific Inc.). Insert and backbone were ligated with T4 DNA ligase (Fermentas Thermo Fisher Scientific Inc.). Before transformation into electrocompetent *E. coli* Top10F' cells, ligation mixtures were desalted with MF Membrane filters. Single colonies from the transformation plates were streaked on LB-Ampicillin (100 µg/mL) agar plates and grown overnight at 37° C. Plasmids (p426GPD_ARE1 and p426GPD_ARE2) were isolated from cell material taken from the agar plates with the Gene Jet Plasmid Miniprep Kit (Fermentas Thermo Fisher Scientific Inc.) according to the manual.

Example 9: Addition of a FLAG-Tag to the HAT-Genes and Cloning into Vector p42GPD In order to add an N-terminal FLAG-tag to the HAT-genes, the genes were amplified from the pHYD-plasmids (heterologous acyltransferases) or p426GPD_ARE1 or p426GPD_ARE2 with the primers listed in Table 7.

PCR products were purified via a preparative agarose gel. After restriction with enzymes BamHI and EcoRI, the PCR-products were ligated with vector backbone of p426GPD and transformed into *E. coli* TOP10F'-cells. Plasmids were isolated from single colony streak outs and correct insertion of the Flag-tagged acyltransferase genes was confirmed by Sanger sequencing.

Example 10: Cloning of kanMX Marker Gene into Vector p426GPD_ScARE2 Instead of URA3 Marker and Recloning of all Flag-Tagged Acyltransferase Genes into p42kanMXGPD Vector with a Kozak Sequence To amplify the vector backbone of p426GPD_ScARE2 (vector sequence without URA3 marker), primer p426GPD_URAfw (Table 7) carrying an overhang with a restriction site for NdeI and primer p426GPD_URArv carrying an overhang with a restriction site for NotI were used. To amplify the kanMX marker gene of plasmid pFA6a_kanMX6, primer NdeI TEFp_fw and primer NotI TEFt_rv were used.

PCR was carried out under following conditions: 50 µL total volume, 200 µM of each dNTP, 0.5 µM of each primer, 50 ng template plasmid DNA, 1 unit Phusion Polymerase (Finnzymes, F-530L) in according Phusion HF Reaction Buffer. Cycling conditions were as follows: 98° C. for 30 s; 30 cycles of 98° C. for 10 s, 61° C. for 30 s, 72° C. for 2:15 min (vector backbone: approx. 7500 bp)/45 s (kanMX marker: approx. 1400 bp); 72° C. for 10 min, finally kept at 4° C.

Amplified DNAs were purified by a preparative agarose gel (Wizard SV Gel and PCR Clean-up System by Promega) and the concentrations were determined after elution. The purified DNA solutions (~45 µL) were digested with FastDigest NotI and FastDigest NdeI (Fermentas Thermo Fisher Scientific Inc.) in respective buffer. After the restriction cut the vector backbone (p42GPD_ScARE2) was dephosphorylated with FastAP Thermosensitive Alkaline Phosphatase. NdeI and NotI digested kanMX marker insert and p426GPD_ScARE2 backbone were purified via SV Minicolumn (Wizard SV Gel and PCR Clean-up System by Promega). For ligation, 100 ng of vector backbone p426GPD_ScARE2 were ligated with kanMX insert using a molar ratio of 1:3 vector to insert with 1 U/µL T4 DNA Ligase (Fermentas Thermo Fisher Scientific Inc.) in appropriate buffer for 1.5 h at room temperature.

The ligation reaction was transformed into electrocompetent *E. coli* Top 10 F' cells. After regeneration in SOC medium the transformation mixture was plated on LB-Ampicillin (100 µg/mL) agar plates. Single colonies from the transformation plates were streaked on LB-Ampicillin (100 µg/mL) agar plates and grown overnight at 37° C. Plasmids were isolated from cell material taken from the agar plates with the Gene Jet Plasmid Miniprep Kit (Fermentas Thermo Fisher Scientific Inc.) according to the manual. The sizes of the plasmids were checked after a control cut with NdeI and NotI on an agarose gel and plasmids showing correct fragment sizes were sent for sequencing to confirm the correct sequence.

For the resulting p42kanMXGPD_ScARE2 vector, the correct sequence of the kanMX6 marker, the 2 p origin, the GAP promoter, and the ARE2 gene was determined.

In order to add a Kozak-sequence (AAA) to the flag-tagged acyltransferase genes (120-124, ARE2) the coding sequences were amplified from the p426GPD_FLAG-ACAT plasmids with the forward primer Kozak-FLAG and the respective reverse primers as shown in Table 7.

The PCR-products were ligated with p426kanMXGPD vector backbone after restriction with enzymes BamHI and EcoRI and transformed into TOP10F'-cells. Plasmids were isolated from single colony streak outs and correct insertion of the acyltransferase genes was confirmed by Sanger-Sequencing. The final constructs, i.e. 2p plasmids, for acyl transferase expression in *S. cerevisiae* are listed below:

P42kanMX_GPD_Sc1
P42kanMX_GPD_Sc2
P42kanMX_GPD_Ca2
P42kanMX_GPD_Tg1
P42kanMX_GPD_Rn1
P42kanMX_GPD_Rn2
P42kanMX_GPD_Pt1
P42kanMX_GPD Example 11: Transformation of Acyltransferase Vectors into Ergosterol, 7-DHC or Cholesterol Producing *S. cerevisiae* are1 are2 Knock-Out Strains Ergosterol producing are1 are2 knock-out strain COS5 (same genotype as COS4 in Table 1 except of matingtype, COS5 is Mata) was transformed with the set of p42kanMX-GPD vectors carrying the homologous and heterologous acyltransferase genes. Transformation was done with the protocol described in Example 9. The same set of vectors was also transformed into the 7-DHC producing are 1 are2 knock-out strain (see Example 3) and the cholesterol producing are 1 are2 knock-out strain (see Example 5). Table 8 gives an overview over the available acyltransferase expressing yeast strains.

TABLE 8

Set of acyltransferase expression strains in strain backgrounds with varying sterol compositions.

| Strain background | Plasmid with acyl transferase |
|---|---|
| Ergosterol producing are1 are2 (COS5) | P42kanMX_GPD_Sc1 |
| | P42kanMX_GPD_Sc2 |
| | P42kanMX_GPD_Ca2 |
| | P42kanMX_GPD_Tg1 |

TABLE 8-continued

Set of acyltransferase expression strains in strain backgrounds with varying sterol compositions.

| Strain background | Plasmid with acyl transferase |
|---|---|
| 7-DHC producing are1 are2 (10A) | P42kanMX_GPD_Rn1 |
| | P42kanMX_GPD_Rn2 |
| | P42kanMX_GPD_Pt1 |
| | P42kanMX_GPD |
| | P42kanMX_GPD_Sc1 |
| | P42kanMX_GPD_Sc2 |
| | P42kanMX_GPD_Ca2 |
| | P42kanMX_GPD_Tg1 |
| | P42kanMX_GPD_Rn1 |
| | P42kanMX_GPD_Rn2 |
| | P42kanMX_GPD_Pt1 |
| | P42kanMX_GPD |
| Cholesterol producing are1 are2 (BA-C) | P42kanMX_GPD_Sc1 |
| | P42kanMX_GPD_Sc2 |
| | P42kanMX_GPD_Ca2 |
| | P42kanMX_GPD_Tg1 |
| | P42kanMX_GPD_Rn1 |
| | P42kanMX_GPD_Rn2 |
| | P42kanMX_GPD_Pt1 |
| | P42kanMX_GPD |

Example 12: Cultivation of Acyltransferase Expressing *S. cerevisiae* Strains Acyltransferase expression strains in 7-DHC- and cholesterol producing-strain background (see Table 8) were cultivated at 28° C. in 250 mL baffled shake flasks for 65 h. 50 mL YPD media containing 100 μM geneticin were inoculated from a preculture to an $OD_{600}$ of 0.1. Cell cultures were fed with 5 mL glucose (20%) after 40 h and again 5 mL after 52 h incubation time. Ergosterol strains were cultivated in the same way but only for 48 h with feeding after 25 and 32 h. For all strains the final $OD_{600}$/mL was measured and samples were taken in volumes containing 10, 20 and 200 OD units of cells. Suspensions were centrifuged at 1500×g for 5 min and cell pellets frozen at −20° C. for further analyses.

Example 13: Gas Chromatography/Mass Spectrometry (GC/MS) Analysis of *S. cerevisiae* Strains with Altered Sterol Pathway with Homologous or Heterologous Acyltransferase Expression from Plasmid The procedure for GC/MS sample preparation and extraction of sterols from whole yeast cells was adapted from Quail and Kelly (1996) and Müllner et al. (2005). Frozen samples of 10 $OD_{600}$ units derived from yeast cultivation were transferred to Pyrex tubes and centrifuged for 5 min at 2500×g subsequently removing the supernatant. Solvent consisting of 0.6 mL methanol, 0.4 mL of 0.5% pyrogallol dissolved in methanol and 0.4 mL of 60% aqueous KOH was added to samples together with 5 μL cholesterol or ergosterol [2 mg/mL] dissolved in ethanol as an internal standard. Suspension was mixed by vortexing and incubated for 2 h at 90° C. in a sand bath or a water bath. Lipids were extracted three times with 1 mL n-heptane upon shaking for 3 min using a Vibrax at 1500 rpm and centrifuged 3 min at 1500 g. Combined extracts were transferred into a second Pyrex tube and taken to dryness under a stream of nitrogen. (Optional: Lipids stored at −20° C.). Lipids were dissolved in 10 μL of pyridine and incubated 30 min for derivatization after adding 10 μL of N,O-bis(trimethylsilyl)-trifluoroacetamide. Samples were diluted with 200 μL of ethyl acetate and transferred to crimp-top vials with micro-inlay.

GC/MS analysis of sialylated sterols was performed with an Agilent 19091S-433 column HP 5-MS (cross-linked 5% phenyl methyl siloxane; dimensions 30 m×0.25 mm×0.25 μm film thickness). Aliquots of 1 μl (syringe size=10 μL) were injected in the split-less mode at 270° C. injection temperature with helium as carrier gas at a flow rate of 0.9 ml/min in constant flow mode for a total run time of 38.67 min. The following temperature program was used: 1 min at 100° C., 10° C./min to 250° C., 3° C./min to 300° C., and 10° C./min to 310° C. Mass spectra were acquired in scan mode. Sterols were identified based on their mass fragmentation pattern, their retention time relative to cholesterol and sterol standards.

Total sterol contents of acyltransferase expressing *S. cerevisiae* strains (see Example 11) after cultivation as described in Example 12 were analyzed by GC/MS, results are given in Table 9, wherein a Quantitative measurement of the total cellular sterols identified by GC-MS detection upon silylation of lipid extracts. Summarized sterol amounts (TOTAL) include precursor molecule squalene (SQL).

TABLE 9

Cellular sterol composition of acyltransferase expression strains. Values are calculated in μg/OD600 relative to cholesterol (ERG- and 7DHC-strains) or ergosterol (CLR-strain) as an internal standard. Percentage values of sterols are relative to TOTAL sterols. Mean values of duplicate measurement (*single). For more explanation, see text.

| | sc1 | Sc2 | Ca2 | Rn1 | Rn2 | Pt1 | Tg1 | ev |
|---|---|---|---|---|---|---|---|---|
| ERG-strain | | | | | | | | |
| TOTAL (μg/$OD_{600}$) | 2.6 ± 0.2 | 2.9 ± 0.1 | 2.2 ± 0.1 | 2.3 ± 0.1 | 1.7 ± 0.0 | 2.1 ± 0.1 | 3.2 ± 0.2 | 2.0 ± 0.1 |
| ERG (%) | 50.5 ± 2.6 | 58.0 ± 2.7 | 57.8 ± 0.3 | 61.1 ± 0.9 | 60.9 ± 1.3 | 60.9 ± 0.6 | 54.0 ± 0.7 | 59.5 ± 1.4 |
| ZYM (%) | 4.3 ± 0.1 | 3.4 ± 0.0 | 3.0 ± 0.1 | | | | | |
| LAN (%) | 7.6 ± 3.0 | 1.3 ± 1.8 | 2.4 ± 0.1 | 1.0 ± 1.4 | 1.1 ± 1.6 | 0.7 ± 1.0 | 3.8 ± 1.4 | 4.6 ± 3.1 |
| SQL (%) | 5.6 ± 0.0 | 6.0 ± 0.2 | 6.2 ± 0.1 | 11.3 ± 0.2 | 9.1 ± 0.3 | 11.3 ± 0.3 | 11.8 ± 0.2 | 12.5 ± 0.4 |
| Other (%) | 32.0 ± 0.3 | 31.3 ± 1.2 | 30.5 ± 0.2 | 26.6 ± 0.3 | 28.9 ± 0.6 | 27.0 ± 0.0 | 30.5 ± 0.9 | 23.4 ± 4.9 |
| 7DHC-strain | | | | | | | | |
| TOTAL (μg/$OD_{600}$) | 3.2 ± 0.0 | 2.7 ± 0.1 | 2.2 ± 0.1 | 1.7 ± 0.3 | 2.3 ± 0.1 | 2.4 ± 0.3 | 2.9 ± 0.2 | 2.0 ± 0.2 |
| 7DHC (%) | 85.5 ± 1.2 | 75.9 ± 0.8 | 74.1 ± 9.3 | 26.9 ± 3.1 | 90.0 ± 0.4 | 90.1 ± 0.3 | 90.5 ± 0.1 | 91.5 ± 0.6 |
| ZYM (%) | 5.1 ± 0.1 | 8.2 ± 0.1 | 14.1 ± 6.3 | 1.3 ± 0.2 | | | | |

TABLE 9-continued

Cellular sterol composition of acyltransferase expression strains. Values
are calculated in μg/OD600 relative to cholesterol (ERG- and 7DHC-strains) or
ergosterol (CLR-strain) as an internal standard. Percentage values of sterols are
relative to TOTAL sterols. Mean values of duplicate measurement (*single). For
more explanation, see text.

|  | sc1 | Sc2 | Ca2 | Rn1 | Rn2 | Pt1 | Tg1 | ev |
|---|---|---|---|---|---|---|---|---|
| LAN (%) | 0.4 ± 0.6 |  | 0.6 ± 0.9 |  |  |  | 0.4 ± 0.0 |  |
| SQL (%) | 1.2 ± 0.3 | 2.7 ± 0.5 | 1.3 ± 0.4 | 1.1 ± 0.4 | 1.2 ± 0.2 | 0.9 ± 1.2 | 0.7 ± 0.0 | 2.4 ± 0.7 |
| Other (%) | 7.8 ± 0.2 | 13.2 ± 0.2 | 9.9 ± 1.7 | 70.7 ± 3.7 | 8.7 ± 0.2 | 9.0 ± 1.6 | 8.4 ± 0.1 | 6.1 ± 0.1 |
| CLR-strain |  |  |  |  |  |  |  |  |
| TOTAL (μg/OD$_{600}$) | 4.7 ± 1.1 | 5.3 ± 0.3 | 6.4 ± 1.7 | 3.8 ± 0.2 | 6.0 ± 0.1 | 3.6* | 6.3 ± 0.7 | 4.2 ± 0.5 |
| CLR (%) | 96.4 ± 0.0 | 98.5 ± 0.0 | 94.2 ± 0.4 | 99.4 ± 0.8 | 96.9 ± 0.3 | 98.3* | 95.4 ± 0.1 | 99.4 ± 0.9 |
| ZYM (%) |  |  | 3.7 ± 0.5 |  |  |  |  |  |
| LAN (%) |  |  |  |  |  |  |  |  |
| SQL (%) |  |  |  |  |  |  |  |  |
| Other (%) | 3.6 ± 0.0 | 1.5 ± 0.0 | 2.1 ± 0.1 | 0.6 ± 0.8 | 3.1 ± 0.3 | 1.7* | 4.6 ± 0.1 | 0.6 ± 0.9 |

Example 14: HPLC Analysis of *S cerevisiae* Strains with Altered Sterol Pathway with Homologous or Heterologous Acyltransferase Expression from Plasmid Biomass pellets of 200 OD units stored at −20° C. in 15 mL Greiner tubes were used for an extraction process: Samples were thawed at room temperature (RT), resuspended in 1 mL zymolyase solution (5 mg/mL in 50 mM KP$_i$ with 1 M D-sorbit) and incubated for 15 min at 37° C. After centrifugation at 3000×g for 5 min, the supernatant was discarded and the pellet was resuspended in 1 mL 100% EtOH. 2.8 mL 100% EtOH and 200 μL internal standard (e.g. 2 mg/mL cholesterylacetate solved in EtOH) was added and mixed in tightly closed tubes at 70° C. with 750 rpm for 1 h. Cooled to RT, tubes were centrifuged at 3000×g for 5 min and subsequently 3 mL of supernatant were transferred to Pyrex glass tubes. The extracts were brought to dryness under N2 and taken up in 200 μL ethyl acetate. Samples were shaken at 40° C. for 15 min to solve lipids, then, unsolved particles were centrifuged at 3000×g for 5 min and the supernatant was transferred to GC vials with inlay. HPLC measurement was performed with a mobile phase containing 80% EtOH 20% MeOH and 0.1% trifluoracetic acid at a flow of 0.6 mL/min. A volume of 10 μL sample was injected at 40° C. Compounds were separated in a YMC-Pack Pro C18 RS column at 20° C. and detected with an UV detector at 210 nm for aromatic structures/sterols in general, 280 nm for sterols with conjugated double bonds such as 7-DHC and ergosterol; alternatively with a MS detector in scan mode and positive SIM at sterol specific masses minus the OH-group (−17). Analysis of HPLC data was done by integrating sterol peaks and normalizing against an internal cholesteryl acetate standard to account for any losses during extraction and, if necessary, data was normalized again to an external cholesteryl acetate standard to adjust results for comparing data of different runs. Free sterol and sterol ester concentrations were both calculated using calibration with free sterol standards.

Free and esterified sterol content of acyltransferase expressing *S. cerevisiae* strains with altered sterol pathway (see Example 11) after cultivation as described in Example 12 were analyzed by HPLC, results are given in FIG. 3. Two main types of sterol esters can be detected which will be esterification products of palmitoleic acid (ester 1) and oleic acid (ester2), the two main fatty acids in yeasts as reported by Zweytick et al. (2000). Additionally, in the ERG-strain, also esters with probably palmitic acid (ester 3) and stearic acid (ester4) were detected.

Example 15: Sterol Pattern of CEN.PK2 Erg5 Erg6 Knock-Out Strain with Our without Expression of 24-Reductase in Combination with ARE1 and/or ARE2 Knock Outs Sterol production in an ergosterol producing CEN.PK2 strain was compared to cholesta-5,7,24 trienol (see Example 1 and 2) or 7-DHC producing strains (see Example 5) with different combinations of are1 and are2 knock-outs. Strains *S. cerevisiae* CEN.PK2, 20B, 2B, 14C (see example 1), COS7, COS8, COS9 (see example 5) were cultivated in triplicates in shake flasks for three days with additional glucose feeding. In order to analyze free sterols and the sterol ester composition of the variants by HPLC ethanolic extracts of 200 OD units were prepared as described in Example 14. Extracts were analyzed by HPLC with UV detection at two wavelengths (210 and 280 nm). Zymosterol compounds were detected by 210 nm UV light, 7-DHC compounds were measured at 280 nm. Concentrations were calculated by relating peak areas to areas detected for 0.5-2 mg/mL standard solutions of zymosterol and 7-DHC. Cholesteryl acetate was used as internal standard to normalize for possible differences within the extraction procedure. For details of HPLC method see Example 14. The sterol composition of the analyzed strains as measured by HPLC analysis is shown in FIG. 4.

Two main types of sterol esters can be detected which will be esterification products of palmitoleic acid (ester 1) and oleic acid (ester2), the two main fatty acids in yeasts as reported by Zweytick et al. (2000).

GC analysis was done from extracts of the same biomass as for HPLC analysis (see FIG. 5). For details of GC analysis see Example 12. Peak areas were integrated and recalculated to amounts in μg per 10 OD units by the internal standard cholesterol (see FIG. 5*b*). FIG. 5A shows the percentage of total sterols.

The invention claimed is:

1. A process for the production of a sterol mix in a yeast cell, said sterol mix comprising 7-dehydrocholesterol (7-DHC) and zymosterol, and said process comprising cultivating said yeast cell under conditions suitable for sterol production, wherein
   (a) the gene encoding the endogenous C22 sterol desaturase (ERG5) and the gene encoding the endogenous Delta(24)-sterol C-methyltransferase (ERG6) have been inactivated in the yeast cell,
   (b) the yeast cell comprises a mutation in the gene encoding Acyl-CoA:sterol acyltransferase 2 (ARE2) that reduces the activity of endogenous ARE2,
   (c) the yeast cell expresses a heterologous enzyme selected from EC 1.3.1.72 having sterol Δ24-reductase activity on lathosterol, zymosterol or trienol, wherein the enzyme EC 1.3.1.72 having sterol Δ24-reductase activity is originated from plant or vertebrate,
   (d) the amount of zymosterol present in the sterol mix is 3% or less based on the total amount of sterols, and
   (e) the percentage of 7-DHC within said sterol mix is at least 87% based on total amounts of sterol in said mix.

2. The process of claim 1, wherein the ratio between the 7-DHC and the zymosterol of at least 87 to 2.

3. The process of claim 1, wherein the sterol mix is a vitamin D3-precursor.

4. The process of claim 3, wherein the sterol mix is 7-DHC.

5. The process of claim 1, the yeast cell further comprises a mutation in the gene encoding Acyl-CoA:sterol acyltransferase 1 (ARE1) that reduces the activity of endogenous ARE1.

6. The process of claim 1, wherein the genes encoding endogenous ARE1 and ARE2 have been inactivated in the yeast cell.

* * * * *

SEQUENCE LISTING

<160> NUMBER OF SEQ ID NOS: 37

<210> SEQ ID NO 1
<211> LENGTH: 40
<212> TYPE: DNA
<213> ORGANISM: Artificial Sequence
<220> FEATURE:
<223> OTHER INFORMATION: primer

<400> SEQUENCE: 1
ctatatggat ccaaaatgac ggagactaag gatttgttgc                    40

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
gactgcgaat tctcataagg tcaggtacaa cgtcataatg                    40

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
gtggcgggta tccagccgcc gaag                                     24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
cttcggcggc tggatacccg ccac                                     24

<210> SEQ ID NO 5
<211> LENGTH: 40
<212> TYPE: DNA
<213> ORGANISM: Artificial Sequence
<220> FEATURE:
<223> OTHER INFORMATION: primer

<400> SEQUENCE: 5
ctatatggat ccaaaatgga caagaagaag gatctactgg                    40

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
gactgcgaat tcttagaatg tcaagtacaa cgtacacatg                    40

<210> SEQ ID NO 7
<211> LENGTH: 73
<212> TYPE: DNA
<213> ORGANISM: Artificial Sequence

```
<220> FEATURE:
<223> OTHER INFORMATION: primer

<400> SEQUENCE: 7
cataatttaa aaaaacaaga ataaaataat aatatagtag gcagcataag atgtctgtta      60
ttaatttcac agg                                                         73

<210> SEQ ID NO 8
<211> LENGTH: 72
<212> TYPE: DNA
<213> ORGANISM: Artificial Sequence
<220> FEATURE:
<223> OTHER INFORMATION: primer

<400> SEQUENCE: 8
ataggtatat atcgtgcgct ttatttgaat cttattgatc tagtgaattt ctatttctta      60
gcatttttga cg                                                          72

<210> SEQ ID NO 9
<211> LENGTH: 71
<212> TYPE: DNA
<213> ORGANISM: Artificial Sequence
<220> FEATURE:
<223> OTHER INFORMATION: primer

<400> SEQUENCE: 9
aaaacatcac attttgctat tccaatagac aataaatacc ttttaacaaa atgtctgccc      60
ctaagaagat c                                                           71

<210> SEQ ID NO 10
<211> LENGTH: 74
<212> TYPE: DNA
<213> ORGANISM: Artificial Sequence
<220> FEATURE:
<223> OTHER INFORMATION: primer

<400> SEQUENCE: 10
taatgaagta aatatgattt attgtctgga caaagttctg ttttccccca ttaagcaagg      60
attttcttaa cttc                                                        74

<210> SEQ ID NO 11
<211> LENGTH: 64
<212> TYPE: DNA
<213> ORGANISM: Artificial Sequence
<220> FEATURE:
<223> OTHER INFORMATION: primer

<400> SEQUENCE: 11
ctataaagat ttaatagctc cacagaacag ttgcaggatg ccgcataggc cactagtgga      60
tctg                                                                   64

<210> SEQ ID NO 12
<211> LENGTH: 64
<212> TYPE: DNA
<213> ORGANISM: Artificial Sequence
<220> FEATURE:
<223> OTHER INFORMATION: primer

<400> SEQUENCE: 12
ctataaagat ttaatagctc cacagaacag ttgcaggatg ccgcataggc cactagtgga      60
tctg                                                                   64
```

```
<210> SEQ ID NO 13
<211> LENGTH: 63
<212> TYPE: DNA
<213> ORGANISM: Artificial Sequence
<220> FEATURE:
<223> OTHER INFORMATION: primer

<400> SEQUENCE: 13
atgacggaga ctaaggattt gttgcaagac gaagagtttc ttaaagcttg cctcgtcccc    60
gcc                                                                  63

<210> SEQ ID NO 14
<211> LENGTH: 65
<212> TYPE: DNA
<213> ORGANISM: Artificial Sequence
<220> FEATURE:
<223> OTHER INFORMATION: primer

<400> SEQUENCE: 14
tcataaggtc aggtacaacg tcataatgat actgggccct gaactggatg gcggcgttag    60
tatcg                                                                65

<210> SEQ ID NO 15
<211> LENGTH: 47
<212> TYPE: DNA
<213> ORGANISM: Artificial Sequence
<220> FEATURE:
<223> OTHER INFORMATION: primer

<400> SEQUENCE: 15
gttgttggat ccaaaaatga tggcttcaga tagagttaga aaaagac                  47

<210> SEQ ID NO 16
<211> LENGTH: 44
<212> TYPE: DNA
<213> ORGANISM: Artificial Sequence
<220> FEATURE:
<223> OTHER INFORMATION: primer

<400> SEQUENCE: 16
caacaagaat tctcatcaga aaatatttgg caataatcta taag                    44

<210> SEQ ID NO 17
<211> LENGTH: 89
<212> TYPE: DNA
<213> ORGANISM: Artificial Sequence
<220> FEATURE:
<223> OTHER INFORMATION: primer

<400> SEQUENCE: 17
aaaacatcac attttgctat tccaatagac aataaatacc ttttaacaaa agtttatcat    60
tatcaatact cgccatttca aagaatacg                                      89

<210> SEQ ID NO 18
<211> LENGTH: 73
<212> TYPE: DNA
<213> ORGANISM: Artificial Sequence
<220> FEATURE:
<223> OTHER INFORMATION: primer

<400> SEQUENCE: 18
taatgaagta aatatgattt attgtctgga caaagttctg tttttcccca ggccgcaaat    60
taaagccttc gag                                                       73
```

<210> SEQ ID NO 19
<211> LENGTH: 62
<212> TYPE: DNA
<213> ORGANISM: Artificial Sequence
<220> FEATURE:
<223> OTHER INFORMATION: primer

<400> SEQUENCE: 19
gcgggatcca tggactacaa agacgatgac gataaagtcg gagaggaaaa gatgtccctg    60
ac                                                                  62

<210> SEQ ID NO 20
<211> LENGTH: 62
<212> TYPE: DNA
<213> ORGANISM: Artificial Sequence
<220> FEATURE:
<223> OTHER INFORMATION: primer

<400> SEQUENCE: 20
gcggaattct cagaaaacgt aacgacaagt ccatgatcta ggcctaacgt aatccagaaa    60
gg                                                                  62

<210> SEQ ID NO 21
<211> LENGTH: 62
<212> TYPE: DNA
<213> ORGANISM: Artificial Sequence
<220> FEATURE:
<223> OTHER INFORMATION: primer

<400> SEQUENCE: 21
gcgggatcca tggactacaa agacgatgac gataaagaac caaaagctcc acaattacgt    60
cg                                                                  62

<210> SEQ ID NO 22
<211> LENGTH: 71
<212> TYPE: DNA
<213> ORGANISM: Artificial Sequence
<220> FEATURE:
<223> OTHER INFORMATION: primer

<400> SEQUENCE: 22
gcggaattct caaggatgac aactccagga tctaggtgtt acaagttccc aaaatgttgg    60
ttgtggtaat g                                                        71

<210> SEQ ID NO 23
<211> LENGTH: 63
<212> TYPE: DNA
<213> ORGANISM: Artificial Sequence
<220> FEATURE:
<223> OTHER INFORMATION: primer

<400> SEQUENCE: 23
gcgggatcca tggactacaa agacgatgac gataaaggat ccaaaatggt aggcgaggaa    60
atg                                                                 63

<210> SEQ ID NO 24
<211> LENGTH: 78
<212> TYPE: DNA
<213> ORGANISM: Artificial Sequence
<220> FEATURE:
<223> OTHER INFORMATION: primer

```
<400> SEQUENCE: 24
gcggaattct caaaacacat atctacaagt ccatgtacgt ggtctgacgt aatcaaggaa        60
agtagggttt ttcaatgg                                                     78

<210> SEQ ID NO 25
<211> LENGTH: 61
<212> TYPE: DNA
<213> ORGANISM: Artificial Sequence
<220> FEATURE:
<223> OTHER INFORMATION: primer

<400> SEQUENCE: 25
gcgggatcca tggactacaa agacgatgac gataaaggca gaactaacac ttctgatcag        60
c                                                                       61

<210> SEQ ID NO 26
<211> LENGTH: 81
<212> TYPE: DNA
<213> ORGANISM: Artificial Sequence
<220> FEATURE:
<223> OTHER INFORMATION: primer$

<400> SEQUENCE: 26
gcggaattct caaaagacca ggtacagagt acagataatg gaagggccag agatgaaacc        60
gaaccaacaa atgatgttac c                                                 81

<210> SEQ ID NO 27
<211> LENGTH: 62
<212> TYPE: DNA
<213> ORGANISM: Artificial Sequence
<220> FEATURE:
<223> OTHER INFORMATION: primer

<400> SEQUENCE: 27
gcgggatcca tggactacaa agacgatgac gataaattag atgatccttt gtctaaaact        60
ag                                                                      62

<210> SEQ ID NO 28
<211> LENGTH: 70
<212> TYPE: DNA
<213> ORGANISM: Artificial Sequence
<220> FEATURE:
<223> OTHER INFORMATION: primer

<400> SEQUENCE: 28
gcggaattct ctcaaaacaa tcttaaaggt tgatgatcgg catgagcatt gtaaaagtgt        60
atttgtgccc                                                              70

<210> SEQ ID NO 29
<211> LENGTH: 60
<212> TYPE: DNA
<213> ORGANISM: Artificial Sequence
<220> FEATURE:
<223> OTHER INFORMATION: primer

<400> SEQUENCE: 29
gcgggatcca aaatggacta caaagacgat gacgataaaa cggagactaa ggatttgttg        60

<210> SEQ ID NO 30
<211> LENGTH: 59
<212> TYPE: DNA
<213> ORGANISM: Artificial Sequence
```

```
<220> FEATURE:
<223> OTHER INFORMATION: primer

<400> SEQUENCE: 30
gctgaattct cataaggtca ggtacaacgt cataatgata ctgggccctg aacagacac      59

<210> SEQ ID NO 31
<211> LENGTH: 60
<212> TYPE: DNA
<213> ORGANISM: Artificial Sequence
<220> FEATURE:
<223> OTHER INFORMATION: primer

<400> SEQUENCE: 31
gcgggatcca tggactacaa agacgatgac gataaagaca agaagaagga tctactggag      60

<210> SEQ ID NO 32
<211> LENGTH: 60
<212> TYPE: DNA
<213> ORGANISM: Artificial Sequence
<220> FEATURE:
<223> OTHER INFORMATION: primer

<400> SEQUENCE: 32
gcggaattct tagaatgtca agtacaacgt acacatgaca cttggtccca tgcagatacc      60

<210> SEQ ID NO 33
<211> LENGTH: 33
<212> TYPE: DNA
<213> ORGANISM: Artificial Sequence
<220> FEATURE:
<223> OTHER INFORMATION: primer

<400> SEQUENCE: 33
aacactacat atgcgtatat ataccaatct aag                                  33

<210> SEQ ID NO 34
<211> LENGTH: 39
<212> TYPE: DNA
<213> ORGANISM: Artificial Sequence
<220> FEATURE:
<223> OTHER INFORMATION: primer

<400> SEQUENCE: 34
ggtggtgcgg ccgccacaga tgcgtaagga gaaaatacc                            39

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
ggtggtcata tgagcttgcc tcgtccccg                                       29

<210> SEQ ID NO 36
<211> LENGTH: 34
<212> TYPE: DNA
<213> ORGANISM: Artificial Sequence
<220> FEATURE:
<223> OTHER INFORMATION: primer

<400> SEQUENCE: 36
ggtggtgcgg ccgcggatgg cggcgttagt atcg                                 34
```

```
<210> SEQ ID NO 37
<211> LENGTH: 40
<212> TYPE: DNA
<213> ORGANISM: Artificial Sequence
<220> FEATURE:
<223> OTHER INFORMATION: primer

<400> SEQUENCE: 37
cgcggatccg cgaaaatgga ctacaaagac gatgacgata                              40
```